United States Patent
Rohayem et al.

(10) Patent No.: US 10,273,484 B2
(45) Date of Patent: Apr. 30, 2019

(54) DOUBLE-STRANDED RNA CONJUGATES AND THEIR USE

(71) Applicant: RiboxX GmbH, Radebeul (DE)

(72) Inventors: Jacques Rohayem, Dresden (DE); Kai Naumann, Radebeul (DE)

(73) Assignee: RiboxX GmbH (DE)

( * ) Notice: Subject to any disclaimer, the term of this patent is extended or adjusted under 35 U.S.C. 154(b) by 0 days.

(21) Appl. No.: 15/129,337

(22) PCT Filed: Mar. 24, 2015

(86) PCT No.: PCT/EP2015/056318
§ 371 (c)(1),
(2) Date: Sep. 26, 2016

(87) PCT Pub. No.: WO2015/144736
PCT Pub. Date: Oct. 1, 2015

(65) Prior Publication Data
US 2017/0107517 A1    Apr. 20, 2017

(30) Foreign Application Priority Data

Mar. 24, 2014 (EP) ..................................... 14161378
May 2, 2014 (EP) ..................................... 14166933

(51) Int. Cl.
| | |
|---|---|
| *A61K 48/00* | (2006.01) |
| *C07H 21/02* | (2006.01) |
| *C07H 21/04* | (2006.01) |
| *C12N 15/117* | (2010.01) |
| *A61K 39/00* | (2006.01) |
| *A61K 39/39* | (2006.01) |
| *A61K 47/60* | (2017.01) |
| *A61K 47/54* | (2017.01) |
| *A61K 47/55* | (2017.01) |
| *A61K 47/68* | (2017.01) |

(52) U.S. Cl.
CPC ............ *C12N 15/117* (2013.01); *A61K 39/00* (2013.01); *A61K 39/39* (2013.01); *A61K 47/54* (2017.08); *A61K 47/545* (2017.08); *A61K 47/551* (2017.08); *A61K 47/554* (2017.08); *A61K 47/60* (2017.08); *A61K 47/6807* (2017.08); *A61K 2039/55583* (2013.01); *C12N 2310/17* (2013.01); *C12N 2310/351* (2013.01); *C12N 2310/3513* (2013.01); *C12N 2310/3515* (2013.01); *C12N 2320/32* (2013.01)

(58) Field of Classification Search
CPC .... C12N 15/113; C12N 15/111; A61K 31/713
See application file for complete search history.

(56) References Cited

FOREIGN PATENT DOCUMENTS

| WO | 2004092191 A2 | 10/2004 |
|---|---|---|
| WO | 2007012329 A2 | 2/2007 |
| WO | 2011009624 A1 | 1/2011 |
| WO | 2012030745 A1 | 3/2012 |
| WO | 2013064584 A1 | 5/2013 |
| WO | 2013097965 A1 | 7/2013 |
| WO | 2014022739 A2 | 2/2014 |

OTHER PUBLICATIONS

Lin et al. (Journal of Virology, 2012, 86, 19, pp. 10359-10369).*
Mian (Journal of Leukocyte Biology, 2013, 94, 1025-1036).*
Ekambar R. Kandimalla, et al., "Conjugation of ligands at the 5'-end of CpG DNA affects immunostimulatory activity" Bioconjugate Chem. 2002, 13, 966-974.
"Synthesis and Properties of Oligonucleotides Carrying Isoquinoline Imidazo[1,2- a ]azine Fluorescent Units"—Sonia Perez-Rentero, et al., Sep. 15, 2010, Bioconjugate Chem, 21, 1622-1628.
"Synthesis of Oligoribonucleic Acid Conjugates Using a Cyclooctyne Phosphoramidite"—Pieter Van Delft, et al., Dec. 3, 2010, Organinc Letters 2010 vol. 12, No. 23, 5486-5489.

* cited by examiner

*Primary Examiner* — Amy H Bowman
(74) *Attorney, Agent, or Firm* — St Onge Steward Johnston and Reens LLC

(57) ABSTRACT

Double-stranded ribonucleic acids (dsRNA) of at least 45 bp, preferably of at least 50 bp, which dsRNA include at least one 5'-triphosphate group and further includes at least one chemical modification at a 5' end, at a 3' end and/or at a non-terminal nucleotide. The invention further provides pharmaceutical compositions containing such modified dsRNAs, methods for their production, and to their use in medicine, in particular for immunostimulation and treatment as well as prevention of infectious, autoimmune, degenerative, cancer and tumor diseases.

27 Claims, 29 Drawing Sheets

| Construct name | Length (bp) | Base content (% (G/C) | Modification | Position of modification |
|---|---|---|---|---|
| RGC75 | 75 | 100 | none | |
| RGC75-3AH | 75 | 100 | aminohexyl | 3' end of rC75 strand |
| RGC75-5AH-BIO | 75 | 100 | aminohexyl-biotin | 5' end of rC75 strand |

Fig. 1

| Construct name | Length (bp) | Base content (% (G/C) | Modification | Position of modification |
|---|---|---|---|---|
| RGC100 | 100 | 100 | none | |
| RGC100-3AH-Bio | 100 | 100 | aminohexyl-biotin | 3' end of rC100 strand |
| RGC100-3AH-Biotin-mAb | 100 | 100 | aminohexyl-biotin-mAb (anti-biotin) | 3' end of rC100 strand |

Fig. 7

DOUBLE-STRANDED RNA CONJUGATES AND THEIR USE

FIELD OF THE INVENTION

The present invention relates to double-stranded ribonucleic acids (dsRNA) of at least 45 bp, preferably of at least 50 bp, which dsRNA comprises at least one free 5'-triphosphate group and further comprises at least one chemical modification at a 5' end, at a 3' end and/or at a non-terminal nucleotide. The invention further provides pharmaceutical compositions containing such modified dsRNAs, methods for their production, and to their use in medicine, in particular for immunostimulation and treatment as well as prevention of infectious, degenerative and tumor diseases.

BACKGROUND OF THE INVENTION

It is known that dsRNA is an agonist of Toll-like receptor 3 (TLR-3), and that RNA, in particular dsRNA, triggers RIG-l-like receptors (RLRs, e.g. MDA-5), in particular RIG-I (retinoic inducible gene I), if a free triphosphate group is present on the RNA. Certain dsRNAs having TLR-3 and RIG-I agonizing activities are disclosed in co-pending International Patent Applications No. PCT/EP2012/071640 and No. PCT/EP2012/071641.

Macrophages and dendritic cells (DCs) take up, e.g. immunomodulatory molecules such as dsRNA by macropinocytosis. However, cells not implicated in mounting an immune response cannot take up dsRNA molecules, and are therefore not amenable for TLR-3 (located in endosomes) or RLRs, more specifically RIG-I (located in the cytoplasm) activation.

SUMMARY OF THE INVENTION

The technical problem underlying the present invention is the provision of improved TLR-3 and/or RLR, in particular RIG-I agonists.

The solution of the above technical problem is provided by the embodiments of the present invention as disclosed in the present description, the claims as well as the appended figures.

In particular, the present invention provides a double-stranded ribonucleic acid (dsRNA) of at least 45, preferably at least 50 bp, optionally (and preferably) comprising at least one free 5'-triphosphate group, and comprising at least one covalent modification at a 3' end, a 5' end and/or a non-terminal nucleotide, said modification having the structure of general formula (I)

wherein X represents a 5'-terminal phosphate group, a 3'-terminal phosphate group or a base of a non-terminal nucleotide of the dsRNA;

$R^1$ is selected from the group consisting of a linear or branched $(C_{1-8})$-alkyl group, a linear or branched $(C_{1-8})$-alkenyl group, a linear or branched $(C_{1-8})$-alkinyl group, $-[O-CH_2-CH_2]_m$ with m being an integer of from 1 to 20, preferably of from 1 to 10, more preferably 3 to 6 such as 3, 4, 5 or 6, and a carbohydrate, each of which may be substituted by one or more substituents selected from the group consisting of hydroxyl, oxo, halogen (preferably Cl, Br of F), cyano, $(C_{1-3})$-alkyl, $(C_{1-3})$-alkylhydroxyl, $(C_{2-3})$-alkenyl and $(C_{2-3})$-alkenylhydroxyl;

Y is selected from the group consisting of $NR^2R^3$, $OR^4$ and $SR^5$;

wherein $R^2$, $R^3$, $R^4$ and $R^5$ are each independently selected from the group consisting of hydrogen and a carrier group enabling the uptake of the dsRNA into a cell, which carrier group is optionally bound via a linker group wherein the carrier group can be bound covalently or non-covalently to the linker, e.g. through Van-der-Vaals and/or hydrogen bonds;

and wherein said covalent modification is not at said at least one free 5'-triphosphate group, if present.

The present invention is also directed to such modified dsRNAs in which, if present, the linker group coupling the carrier group as defined above is not yet bound to a carrier.

In further aspects of the invention, the dsRNA modified as disclosed herein may be a species having one or more single-stranded overhangs at the 5' and/or 3' end(s). The modification as disclosed herein may also be present at such an overhang, or, generally speaking, at a single-stranded section present at the 3' end and/or 5' end of the respective species.

According to preferred embodiments of the invention $R^1$ is selected from hexyl which can optionally (preferably when X in formula (I) is a 3'-terminal phosphate group of the dsRNA) be substituted with $-(C_{1-3})$-alkylhydroxyl, preferably methylhydroxyl ($-CH_2OH$), and $-[O-CH_2-CH_2]_3$.

In a preferred embodiment one of $R^2$ and $R^3$ in $NR^2R^3$ is hydrogen. In preferred embodiments of this type, the other group of $R^2$ and $R^3$ is a linker (or spacer group) selected from 6-aminocaproyl, 6-caproylamido-6-caproyl, $-[O-CH_2-CH_2]_y$, with y being an integer selected from 3,4,5,6,7,8,9,10,11, and 12, more preferably 4 or 11, which linker group is preferably bound to a biotin group.

In a preferred embodiment $R^2$ and $R^3$ in $NR^2R^3$ are hydrogen.

In a preferred embodiment, the carrier is selected from other nucleic acid moieties which may be deoxyribonucleic acids, ribonucleic acids or mixtures thereof, aptamers, polyethylenglycol such as PEG groups having an average molecular weight of from about 500 to about 1000 Da, e.g. about 750 Da, peptides, a palmitoyl group, cholesterol groups, phospholipids, proteins such as antibodies, and partners of non-covalent binding pairs such as biotin or digoxigenin. In the case of biotin, it can serve for associating the construct to a streptavidin group present on an antibody, or the biotin may serve as the ligand of an anti-biotin antibody which may, e.g. in turn have a second affinity to a target cell or tissue such as by having an affinity to a target receptor and/or ligand expressed intracellular and/or on the surface of the target cell and/or tissue. Antibody conjugated dsRNA constructs of the invention provide an "antibody-RNA-conjugation" (ARC) strategy.

Antibodies in the context of the present invention, in particular in the context of the ARC strategy, may be selected from polyclonal, monoclonal, humanized, chimeric, single-chain antibodies and antibody fragments which antibodies or antibody fragments may be single-specific or bispecific species. The antibody fragment may be a Fab fragment, a F(ab')$_2$ fragment, or any fragment that retains the antigen-binding specificity of the intact antibody. Especially preferred antibody ligands that may be coupled to the dsRNA are selected from antibodies or fragments thereof directed against cancer and/or tumor antigens, cancer- and/or tumor-associated antigens or oncoproteins, or antigens present on non-cancer and/or non-tumoral cells.

In other embodiments of the invention, a dsRNA as defined herein may be complexed with other entities enabling the entry of the dsRNA into cells such as, e.g., poly(C)ationic compounds such as protamine or poly-L-lysine, and liposomes, in particular cationic liposomes.

Particularly preferred modifications at a 3' end of dsRNAs according to the invention are selected from the following structures:

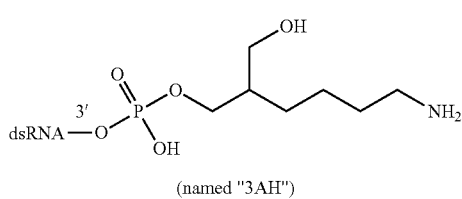

(named "3AH")

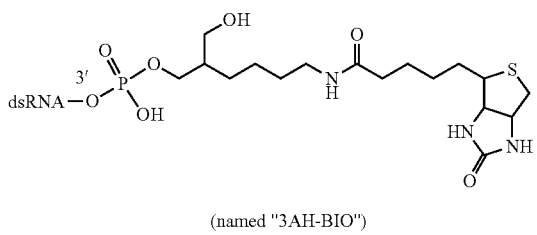

(named "3AH-BIO")

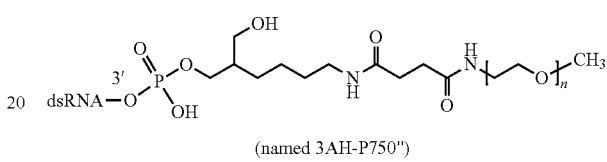

(named 3AH-P750")

wherein n in formula (IV) is an integer of at least one such as 4 to 12, more preferably n is selected such that the polyethylene glycol (PEG) group has an average molecular weight of from about 500 Da to 1000 Da, particularly preferred of about 750 Da.

Particularly preferred modifications at a 5' end of dsRNAs according to the invention are selected from the following structures:

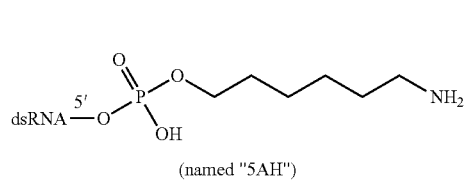

(named "5AH")

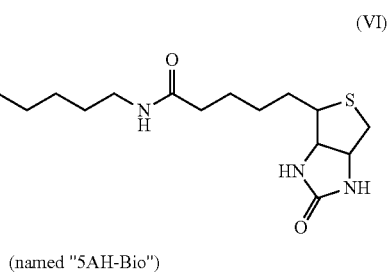

(named "5AH-Bio")

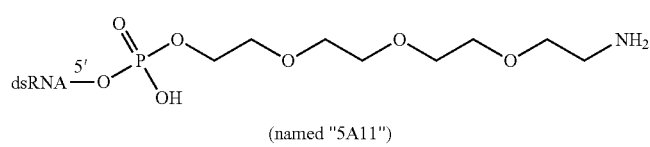

(named "5A11")

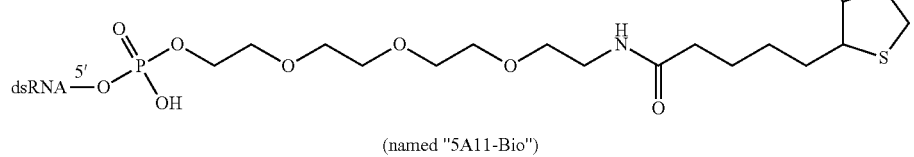

(named "5A11-Bio")

Other especially preferred modifications at a terminal phosphate group of the dsRNA of the invention are selected from the structures according to following formulas (IX) to (XI):

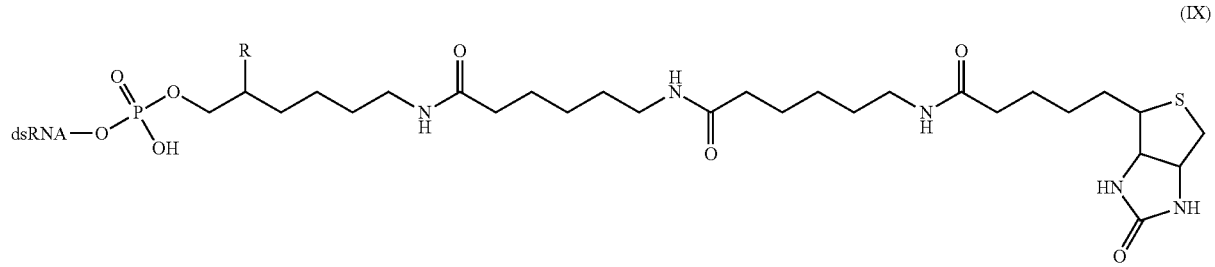

(IX)

(named "3-LCLC-Bio" (in case the phosphate group is a 3'-terminal phosphate group, or "5-LCLC-Bio" (in case the phosphate group is a 5'-terminal phosphate group)) wherein R is selected from H and —CH$_2$OH, preferably R is H, if the phosphate group is a 3'-terminal phosphate group, and preferably R is —CH$_2$OH, if the phosphate group is a 5'-terminal phosphate group;

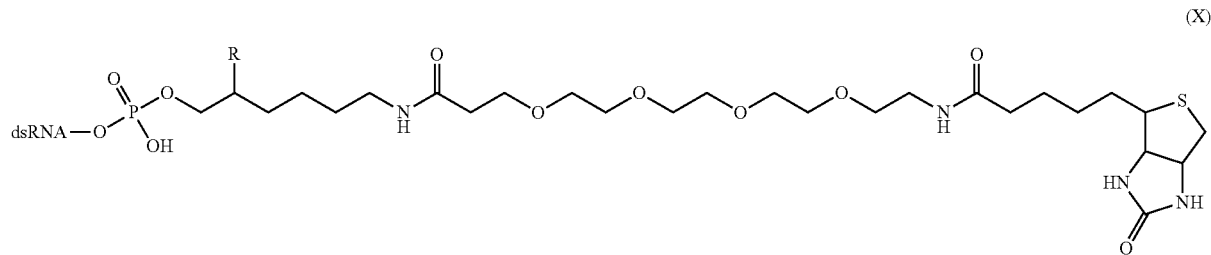

(X)

(named "3-TEG-Bio" (in case the phosphate group is a 3'-terminal phosphate group, or "5-TEG-Bio" (in case the phosphate group is a 5'-terminal phosphate group)) wherein R is selected from H and —CH$_2$OH, preferably R is H, if the phosphate group is a 3'-terminal phosphate group, and preferably R is —CH$_2$OH, if the phosphate group is a 5'-terminal phosphate group;

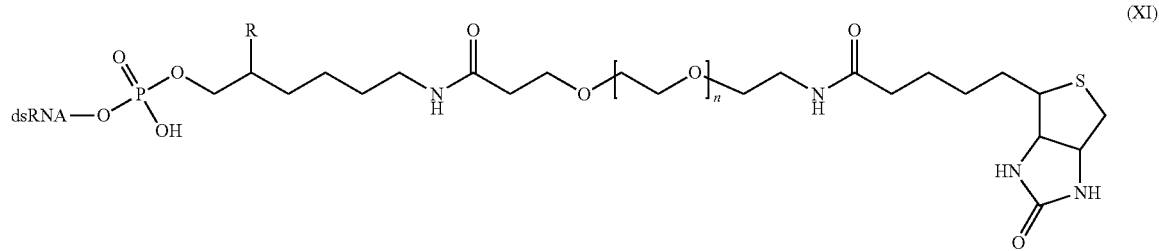

(XI)

(named "3-PEG12-Bio" (in case the phosphate group is a 3'-terminal phosphate group, or "5-PEG12-Bio" (in case the phosphate group is a 5'-terminal phosphate group)) wherein R is selected from H and —CH$_2$OH, preferably R is H, if the phosphate group is a 3'-terminal phosphate group, and preferably R is —CH$_2$OH, if the phosphate group is a 5'-terminal phosphate group;

Especially, if a more voluminous carrier group (e.g. a PEG group, an antibody, in particular in the context of an ARC strategy, etc.) is present on the modified dsRNA according to the invention, it is preferred that the modification according to above formula (I) is present at a 5' phosphate group while preferably the 5' end of the other strand of the dsRNA bears a free 5' triphosphate group. As shown in the Examples below (see, e.g. FIG. 27) this arrangement provides for optimal induction of cytokines/chemokines by the dsRNA through TLR-3 and RLR, in particular RIG-I, activation.

The dsRNA portion of the inventive constructs is, besides the presence of at least 45, 46, 47, 48 or 49 bp, most preferred at least 50 bp, and optionally the presence of a free 5' triphosphate group, but it is understood that the dsRNA useful in the present invention has preferably no marked complementary to a gene or mRNA sequence, in particular it is desired that it does not lead to RNA interference. More specifically, the dsRNA of the invention is not a siRNA (or a molecule leading to RNAi such as a dsRNA processed in a cell to a siRNA). Furthermore, the dsRNA of the present invention may be composed of a self-complementary single RNA strand or of two non-covalently linked, complementary (or at least partially complementary) RNA strands. Most preferred are dsRNAs made of two complementary RNA strands of at least substantially equal length.

Preferred dsRNAs of the invention (i.e. the dsRNA forming the basis of the modified dsRNA) are those disclosed in International Patent Applications No. PCT/EP2012/071640 and No. PCT/EP2012/071641. In particular, it is referred to subject matter as defined in any one of claims 1, 2, 3, 4, 5, 6, 7, 8, 9, 10, 11, 12, 13 and/or 14 of PCT/EP2012/071640 and the respective description thereof on page 2, line 8, to page 9, line 11. Furthermore, it is referred to the subject matter as defined in any one of claims 1, 2, 3, 4, 5, 6, 7, 8, 9, 10, 11 and/or 12 of PCT/EP2012/071641, as well as the respective description thereof on page 1, line 19, to page 8, line 33.

In certain preferred embodiments of the invention, the dsRNA is selected from the group consisting of poly(G):poly(C) and poly(G/I):poly(C), optionally containing one or more modified or unmodified nucleotides such as, e.g., one or more 5-amino-allyl uridine residue(s).

In particular, poly(G/I):poly(C) species of use for providing modified dsRNAs of the invention are dsRNAs having a length of at least 45 bp wherein one strand is polycytidylic acid (poly(C)). In other embodiments this strand is substantially composed of cytosine residues, i.e. there may be a low number of other nucleotides such as not more than 10% of the nucleotides in this strand. The other strand being complementary to the poly(C) (or substantially poly(C)) strand has a nucleotide sequence composed of guanosine (G) and inosine (I) residues according to the formula $(G)_{1\ to\ (n-1)}:I_{(n-1)\ to\ 1}$, preferably $(G)_{10\ to\ (n-10)}:I_{(n-10)\ to\ 10}$, i.e. the complementary strand has from 1 to n-1 G residues, preferably 10 to n-10 G residues (n being the total number of nucleotides in the complementary strand or length of the dsRNA, respectively), and the respective remainder are I residues, or vice versa, whereby the G and I residues can be present in any sequence, i.e. the G and I residues can be located at any position within the sequence of the complementary strand. In case, the first strand is not pure poly(C) the complementary strand has complementary nucleotides in those positions in which on the first strand a non-cytosine residue is present whereas the remaining residues of the complementary strand comply with the above formula (wherein in this case n is the number of C residues in the first strand). In further preferred embodiments, the complementary strand of dsRNAs of the invention has an inosine content of from about 1 to about 99%, more preferably about 5 to about 95%, most preferred from about 10 to about 80%.

In preferred embodiments of this type of dsRNA, the strand complementary to the poly(C) strand contains more I residues than G residues, e.g. the ratio of G to I residues in the complementary strand is about 1:2 or lower such as about 1:3, about 1:4 or about 1:5. In other preferred embodiments of this type, the inosine content in the complementary strand is about 51 to about 90 %, particularly preferred about 60 to about 80 %.

Poly(G):poly(C) dsRNAs of the invention are preferably produced by first providing the desired poly(C) strand, e.g. through chemical synthesis, then the poly(C) strand is modified at the desired group (3' phosphate, 5' phosphate, or internal base), e.g. by introducing a moiety that contains an amino group (see e.g. above structures (II), (V) and (VII), and then enzymatically synthesizing the complementary poly(G) strand using an RNA dependent RNA polymerase (RdRp) of a calicivirus, typically as described in WO-A-2007/012329. The modification can then be further extended as desired (e.g. by binding a biotin group, digoxigenin group or PEG to the amino moiety; see e.g. above formulas (III), (IV), (VI), (VIII), (IX), (X) and (XI), respectively). Ultimately, the thus-produced construct can be coupled to a carrier, preferably an antibody (e.g. an anti-biotin antibody which may have a second affinity, e.g. for a target cell or tissue such as by having an affinity to a target receptor and/or ligand expressed intracellular and/or on the surface of the target cell and/or tissue.).

Besides the lower length limit with respect to the TLR-3 agonistic activity (i.e. at least 45 bp, more preferably at least 46 bp, more preferably at least 47 bp, more preferably at least 48 bp, more preferably at least 49 bp, and most preferably at least 50 bp), the length of the dsRNA (or, in other embodiments, the length of the double-stranded section of the RNAs as defined herein) is not critical. Particularly preferred dsRNAs (or the double-stranded segment) have a length of from 50 to 200 bp, most preferably, the species have a length of 50 bp, 75 bp, 100 bp, 150 bp or 200 bp.

Most preferred dsRNA species of the invention are poly(G):poly(C) species of 75 or 100 bp modified by the structures selected from above formulas (II) to (XI), preferably at the poly(C) strand, e.g. at the 5' phosphate, preferably as shown in above formulas (V) to (XI). Especially preferred examples are outlined in FIG. 1 and FIG. 7 as well as in Example 1. In further preferred embodiments, the biotin group present in structures (III), (VI) and (VIII) to (XI) is coupled to an antibody (antibody-RNA-conjugation strategy, ARC) such as a streptavidin-conjugated antibody or an anti-biotin antibody. In general, the constructs outlined in Example 1 are highly preferred.

In the present invention, the carrier may bind to one or more such as preferably 2, 3, 4 or 5 dsRNAs (such as a bispecific antibody bearing two binding sites for said dsRNAs).

The present invention is also directed to compositions of at least two different modified dsRNA molecules as disclosed herein. In this respect, the different molecules may have different dsRNAs (such as different lengths, sequences, base compositions etc.) and/or different modifications as defined herein.

The dsRNAs of the present invention may also contain one or more modified nucleotide analogues, in particular with respect to stability considerations and/or for providing the anchor point of the modification according to formula (I).

The chemical modification of the nucleotide analogue in comparison to the natural occurring nucleotide may be at the ribose, phosphate and/or base moiety. With respect to molecules having an increased stability, especially with respect to RNA degrading enzymes, modifications at the backbone, i.e. the ribose and/or phosphate moieties, are especially preferred.

Preferred examples of ribose-modified ribonucleotides are analogues wherein the 2'-OH group is replaced by a group selected from H, OR, R, halo, SH, SR, $NH_2$, NHR, $NR_2$, or CN with R being $C_1$-$C_6$ alkyl, alkenyl or alkynyl and halo being F, Cl, Br or I. It is clear for the person skilled in the art that the term "modified ribonucleotide" also includes 2'-deoxyderivatives, such as 2'-O-methyl derivatives, which may at several instances also be termed "deoxynucleotides".

As mentioned before, the at least one modified ribonucleotide may be selected from analogues having a chemical modification at the base moiety. Examples of such analogues include, but are not limited to, 5-aminoallyl-uridine, 6-aza-uridine, 8-aza-adenosine, 5-bromo-uridine, 7-deaza-adenine, 7-deaza-guanine, $N^6$-methyl-adenine, 5-methyl-cytidine, pseudo-uridine, and 4-thio-uridine.

Examples of backbone-modified ribonucleotides wherein the phosphoester group between adjacent ribonucleotides is modified are phosphothioate groups.

Further subject matter of the invention is a method for the preparation of a dsRNA according to any one of the preceding claims comprising the step of coupling the group $R_1$—Y as defined above in formula (I) to a 5'- terminal phosphate group, a 3'-terminal phosphate group or a base of a non-terminal nucleotide of the dsRNA.

The preparation of modified dsRNAs is generally known in the art. Procedures for corresponding chemistries can be taken from, e.g. Bramsen and Kjems (2011) Methods Mol. Biol. 721:77-103, or Hermanson G. T. (2008). *Bioconjugate Techniques.* 2nd Edition. Academic Press, San Diego.

In certain embodiments, a terminal phosphate group, especially a 5' phosphate group of a basic dsRNA, or of one strand thereof is derivatized by the EDC method using, e.g. a primary amine or primary diamine (see e.g. Hermanson G. T. (2008), supra, pp. 969-1002).

Amine-modified phosphate groups of RNAs (see, e.g. formula (II) and (v), respectively) can further be subjected to reactions introducing a carrier such as biotin, e.g. using NHS-biotin typically resulting in structures like those shown in formulas (III), (VI) and (VIII). In further embodiments it may be desired to introduce longer spacer moieties between the amine linked to the terminal phosphate and the carrier, e.g. biotin. In the case of biotin, one can use, e.g. NHS-PEG-biotin (wherein the length of the PEG moiety can vary in a broad manner; cf., e.g., formulas (X) and (XI), NHS-LC-biotin or NHS-LCLC-biotin (see, e.g., formula (IX)). Suitable biotinylation reagents are commercially available, e.g. from Thermo Fisher Scientific Inc., Rockford, Ill., USA. NHS esters are not only available for biotin, but for a variety of carriers such digoxigenin and PEGs.

Coupling of TLR-3 and/or RLR, specifically RIG-I, agonists to a carrier entity as provided in the present invention for delivery to non-immune cells has important implications in the fields of immunostimulation for treatment of degenerative diseases, infections, autoimmune disorders and cancer, and the present invention relates to the treatment of such diseases using the dsRNAs as defined herein using corresponding pharmaceutical compositions.

Other dsRNAs of the invention wherein the group $R^1$—Y of above formula (I) does in itself not yet include a carrier provide further special benefits in that these species cannot be taken up by cells that are not capable of macropinocytosis which are therefore not activated. This is of great medical relevance, because, when targeting, e.g. cancer cells by TLR-3 agonists to induce apoptosis, non-activation of not targeted cells such as cells (such as plasmacytoid and/or myeloid dendritic cells, macrophages, monocytes, natural killer (NK) cells, T CD4+ lymphocytes, T CD8+ lymphocytes, B lymphocytes) implicated in the immune response, e.g. an innate immune response or an adaptive immune response, is mandatory for safety and toxicity issues. In this case, when considering a composition of a dsRNA coupled to a carrier as defined herein such as an aptamer or a mAb, such compositions typically contain (since the coupling is almost never complete):

conjugated carrier+TLR-3/RLR (particularly RIG-I) agonist carrier alone modified TLR-3/RLR (particularly RIG-I) agonist not coupled to carrier.

When injected into the body system, it is mandatory to ensure that the active substance (here the TLR-3/RLR (particularly RIG-I) agonist as defined herein) is delivered to the targeted cell and preferably only there. In the case of the present invention, because the modified TLR-3/RLR (particularly RIG-I) agonist not coupled to the carrier is not taken up by cells implicated in the immune response, there will be no activation of these cells, and hence the effect will be specific to the targeted cells only, or at least substantially only to the target cells.

In consideration of the improved properties of the dsRNAs according to the invention, the present invention is, as already mentioned above, also directed to a pharmaceutical composition comprising the dsRNA as defined herein in combination with at least one pharmaceutically acceptable carrier, excipient and/or diluent.

Thus, the dsRNAs or compositions of such dsRNAs as defined or disclosed above are particularly for use as agonists of TLR-3. Further preferred dsRNAs of the invention containing a free 5'-triphosphate moiety are also agonists of RIG-I-like receptors (RLRs), in particular of RIG-I and/or other RLRs. In that function, the RNA molecules of the present invention exert an immunostimulatory effect in immune and non-immune cells or organisms. dsRNAs and their compositions according to the present invention are therefore useful as medicaments, in particular immunostimulatory preparations. dsRNAs and compositions thereof according to the invention are also contemplated for the manufacture of a medicament for immunostimulation. The preparation of pharmaceutical compositions in the context of the present invention, their dosages and their routes of administration are known to the skilled person, and general guidance can be found in the latest edition of Remington's Pharmaceutical Sciences (Mack Publishing Co., Eastern, Pa., USA).

Preferred pharmaceutical compositions are injectable solutions containing the dsRNAs or their compositions as defined above, optionally in combination with one or more antigens of interest, and, if desired or required, further adjuvants or other typical components of immunostimulatory preparations, in (preferably pyrogen-free) water, isotonic aqueous media (such as Ringer lactate or isotonic NaCl solution) or buffer to provide the appropriate pH value.

In cases where the RNA of the invention is used as an immunostimulatory drug alone, a topical administration of the appropriate preparation (e.g. a spray or an injectable solution) to skin and/or mucosa is preferred. As an active pharmaceutical ingredient (API) also termed "RNA drug" the RNA of the present invention leads to stimulation of antigen-presenting cells such as dendritic cells, monocytes and macrophages and generation of a Th2 and/or Th1 immune response including a CD8+ T cell response, natural killer (NK) cell response and/or B cell response leading to antibody production. Such stimulation of immune and/or non-immune cells typically leads to the induction of cytokine expression such as of type I and/or type II IFN production, and/or of TNF-α and/or IL1-β and/or IL-6 and/or induction of chemokine expression such as of IP-10 and/or MCP-1 and/or RANTES and/or 1-TAC and/or GRO-α. This application of the inventive dsRNA as an API is especially useful in the treatment of infectious diseases, e.g. by viruses (such as Herpesvirus, Papillomavirus), bacteria, parasites or fungi, or in the treatment of autoimmune diseases, degenerative diseases and/or cancer.

The improved immunostimulatory effects of the double-stranded ribonucleic acids of the present invention as well as their compositions as defined herein are especially useful in therapeutic or prophylactic vaccine preparations directed to a certain disease. Thus, the dsRNA and compositions of the invention may also be used as an "RNA adjuvant" or "Immunoadjuvant" in vaccine preparations or therapeutic vaccine applications (or administered in a distinct preparation together with the vaccine or antigen, respectively, or sequentially). Accordingly, preferred pharmaceutical compositions of this aspect further comprise an antigen of interest to generate a specific immune response (antibody response or cellular immune response, i.e. CD8+ T cell response against the cells expressing the antigen and/or NK cell response, against the antigen), optionally together with a further adjuvant known in the art. Simultaneous or sequential administration of the antigen/vaccine and the immunostimulatory dsRNA or compositions of the present invention should improve the immune response against the antigen of the vaccine by generating a protective CD8+ T cell response to the cells expressing soluble proteins (antigens) and/or NK cell response, triggering DC, macrophage and/or monocyte activation and induction of cytokine expression such as of type I and/or type II I FN production, and/or of TNF-α and/or IL1-β and/or IL-6 and/or induction of chemokine expression such as of IP-10 and/or MCP-1 and/or RANTES and/or l-TAC and/or GRO-α.

Accordingly, the present invention relates also to methods for induction of cytokines/chemokines, in particular induction of type I and/or type II IFN production, and/or of TNF-α and/or IL1-β and/or IL-6 and/or IP-10 and/or MCP-1 and/or RANTES and/or I-TAC and/or GRO-α in non-immune cells, preferably in tumor and/or cancer cells, endothelial cells and/or neuronal cells, or in immune cells, especially DCs, macrophages and/or monocytes, in vitro or in vivo, in particular when present in a subject, preferably a mammal, more preferably a human, especially when in need for such induction of such cytokines/chemokines.

The induction of, e.g. IP-10, in tumor and/or cancer cells and other non-immune cells such as endothelial cells can be used for various applications such as the treatment of tumors and/or cancers by hindering or impeding neo-angiogenesis in the tumor/cancer through IP-10 secretion. In preferred embodiments of this type of application, the dsRNA constructs of the invention are preferably equipped with an antibody directed to endothelial cells present in blood vessels, in particular in the vicinity of a tumor, which then prevent blood supply to the tumor due to the expression of IP-10 hindering or preventing neo-angiogenesis towards the tumor. Furthermore, IP-10 is an important trigger of integrin and selectin expression, and plays an important role in T cell recruitment. Further applications include the treatment of diabetic neuropathy, especially ophthalmic appearances of diabetic neuropathy, as well as acute macular degeneration (acute macular neuroretinopathy), or various autoimmune disorders.

The double-stranded ribonucleic acids or pharmaceutical compositions as disclosed herein can also be combined with further immunostimulatory drugs known in the art such as other TLR agonists (including, but not limited to, agonists of TLR-5, TLR-7, TLR-8 and/or TLR-9) and or RLR agonists such as agonists of MDA-5 and/or (and preferably) of RIG-I.

The ribonucleic acids of the present invention are particularly useful in the treatment of diseases, including infectious diseases caused by infectious agents such as bacteria, viruses, parasites and fungi, cancer and/or tumors as well as degenerative diseases such as neurodegenerative disease, e.g. diabetic neuropathy, or acute macular degeneration (acute macular neuroretinopathy), or various autoimmune disorders.

The present invention also provides a method for the treatment of a disease as mentioned above, preferably a viral infection or a cancer and/or tumor disease, comprising administering an effective amount of the pharmaceutical composition of the invention to a preferably mammalian, particularly human, subject in need of such treatment.

Administration routes for pharmaceutical compositions as defined herein, and in the context of medical treatments which may be prophylactic or therapeutic, include subcutaneous, intro-ocular, intra-cerebral, intra-spinal, intra-dermal, intra-muscular, intra-peritoneal and/or intra-venous injection in a single or repeated dose, optionally combined with an antigen and/or immunogenic peptide, further optionally combined with another adjuvant that may be present in a depot form (such as an Aluminium salt), or combined with a further activator of innate immunity such as agonists of toll-like receptor 1 to 10 (TLR-1 to TLR-10) and/or of RLRs (such as MDA-5) and/or specifically of RIG-I. Preferred examples of further TLR-3 agonists are disclosed in, e.g. WO-A-2013/064584 and Naumann et al. (2013) Clinical and Developmental Immunology, available under the URL http://www.hindawi.com/journals/cdi/2013/283649/.

It is also contemplated to provide the dsRNAs or compositions thereof and antigens and/or additional adjuvants in separate same or different formulations and to administer these formulations to the patient separately, e.g. by injection such as intra muscular injection, at the same of different locations, e.g. the inventive dsRNA or composition thereof at one location, and the antigen and/or additional adjuvant at a different location.

In general, a suitable dose of dsRNAs of the invention will be in the range of 0.001 to 500 mg per kilogram body weight of the subject per day, typically about 10 μg per kg to about 500 mg per kg, preferably about 100 μg per kg to about 100 mg per kg such as about 1 mg per kg to about 75 mg per kg, or about 10 mg per kg to about 50 mg per kg, or about 1 μg per kg to about 50 μg per kilogram body weight of the subject to be treated. The pharmaceutical composition may be administered once per day, or the dsRNA(s) may be administered as two, three, four, five, six or more sub-doses at appropriate intervals per day. The skilled person understands that in case of multiple doses per day, the individual dose must be adapted to reach the selected daily dose.

The dosage unit can also be adapted for delivery over more than one day, e.g. using conventional sustained release formulations known in the art, which provide a sustained release of the dsRNA(s) over the selected period such as over two or more days. In such embodiments, the dosage unit typically contains a corresponding multiple of the chosen daily dose of the dsRNA(s).

The present invention also relates to a cell or non-human organism being transfected, transduced or transformed with the double-stranded RNA molecules or compositions such as antibody-RNA-conjugates (ARC) as defined herein.

Studies of the mechanism of action of improved combined TLR-3/RLR (specifically RIG-I) antagonist according to the invention (see FIGS. 21 and 22 and their respective legend below) imply that dsRNAs of the invention can be used to target desired cells such as tumor and/or cancer cells orendotherial cells using, e.g. appropriate carrier molecules such as antibodies (antibody-RNA-conjugates, ARC), for introducing the dsRNAs into the target cells which then express TLR-3 on their surface that can again be targeted by dsRNAs of the invention or other TLR-3 agonist that do not need a carrier molecule, since TLR-3 molecules present on the surface of the cells can be reached by TLR-3 agonists present outside the cells (e.g. in the blood stream); see also the Examples. Thus, according to the invention less molecules having carrier molecules are needed compared to corresponding therapeutic regimen that have been proposed in the prior art.

The present invention is further illustrated by the following examples and appended drawings.

BRIEF DESCRIPTION OF THE DRAWINGS

The figures show:

FIG. 1: shows a table summarizing the properties of preferred dsRNAs of the invention. The first compound (RGC75) is unmodified $(G:C)_{75}$ used as a comparative example.

FIG. 7: Table summarizing the properties of preferred dsRNAs of the invention. The first compound (RGC100) is unmodified $(G:C)_{100}$ used as a comparative example.

Tfx: cells incubated with transfection reagent alone. The indicated chemokines were measured in the cell culture supernatant by ELISA.

FIG. 17 Expression of TLR-3, E-selectin, ICAM-1 and VCAM-1, respectively, in HUVECs upon transfection with poly(G):poly(C) compound. HUVECs were seeded in 24-well plates at $5\times10^4$ cells/well, and incubated with (G:C)$_{100}$ RNA (RGC) at 3 µg/ml in the presence of the transfection reagent (Tfx) riboxx® FECT (RiboxX GmbH, Radebeul, Germany) according to the manufacturer's instructions. The filled gray curves correspond to basal expression in HUVECs, the dotted lines to HUVECs incubated with riboxx® FECT alone, and the continuous lines to HUVECs incubated with RGC and riboxx® FECT. Measurements were done by FACS in a commercially available cell sorter (CUBE, Partec GmbH, Meckenheim, Germany). (A) Endosomal TLR-3 at 4 hours post transfection. (B) Surface TLR-3 at 4 hours post transfection. (C) E-selectin at 4 hours post transfection. (D) ICAM-1 at 24 hours post transfection. (E) VCAM-1 at 48 hours post transfection.

Figure 18:
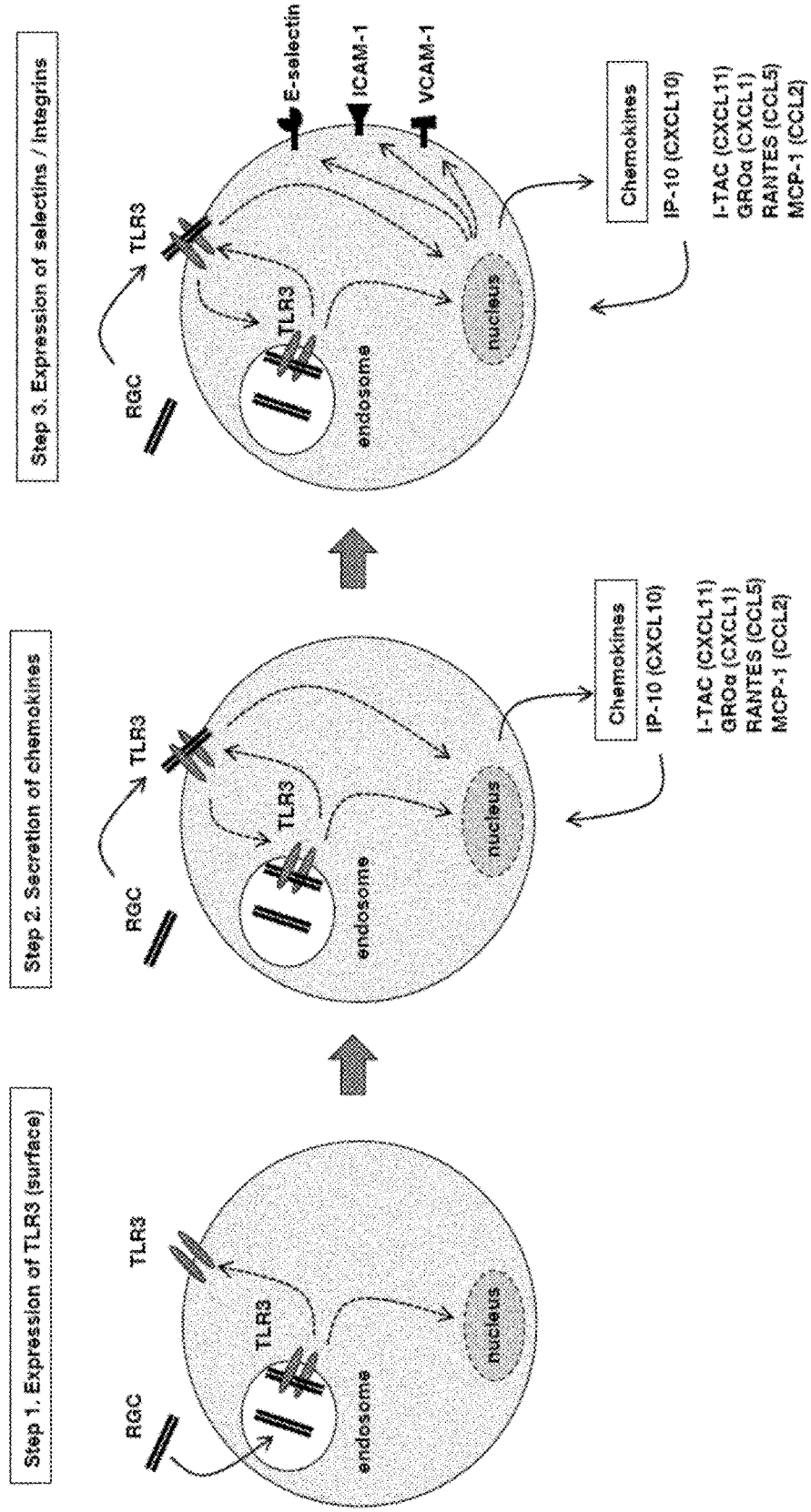

FIG. 18 Schematic representation of the mechanism of activation of HUVEC by poly(G):poly(C) compounds (RGC).

Figure 19:
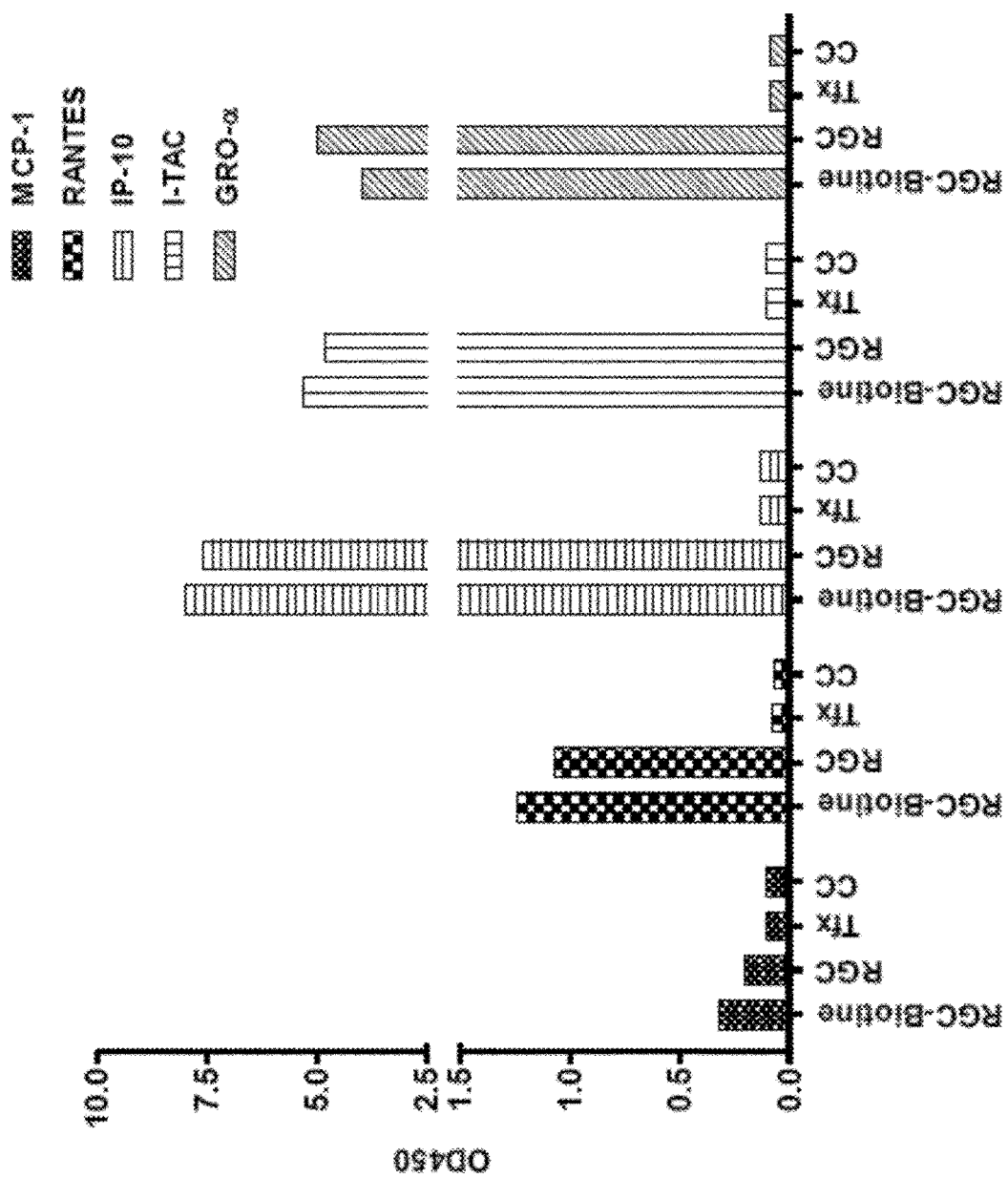

FIG. 19 Activation of HUVECs by a modified poly(G):poly(C) compound according to the invention. HUVECs were seeded in 24-well plates at $5\times10^4$ cells/well, and incubated with (G:C)$_{75}$ RNA or biotinylated (G:C)$_{75}$ RNA (RGC-Biotine) at 6 µg/ml in the presence of the transfection reagent (Tfx) riboxx® FECT (RiboxX GmbH, Radebeul, Germany) according to the manufacturer's instructions. The mean results of two independent measurements for each cytokine are shown. CC: cell culture supernatant as negative control. Tfx: cells incubated with transfection reagent alone. The indicated chemokines were measured in the cell culture supernatant by ELISA.

Figure 20:
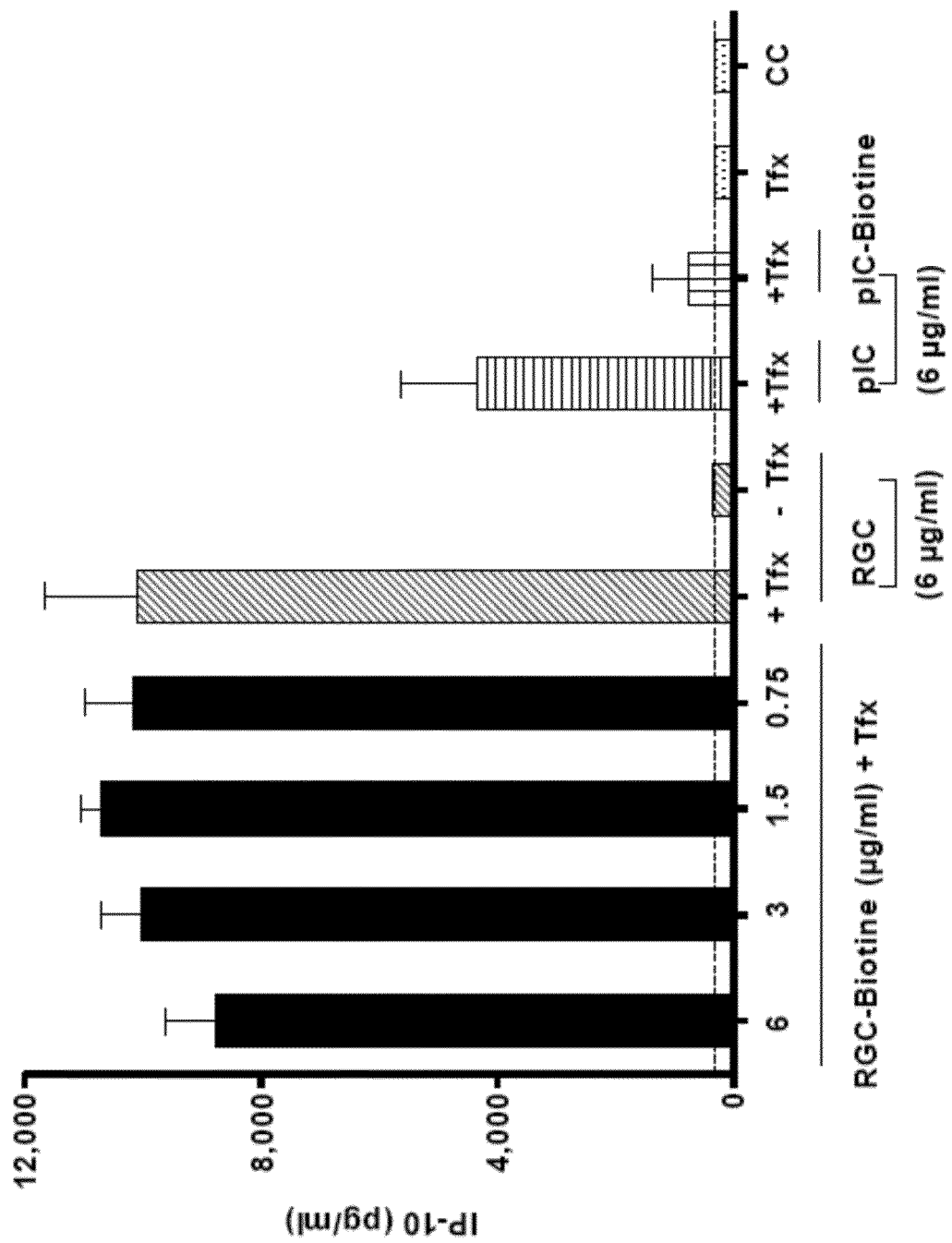

FIG. 20 Comparison of activation of HUVECs by a modified poly(G):poly(C) compound according to the invention and poly(I:C). HUVECs were seeded in 24-well plates at $5\times10^4$ cells/well and incubated with unmodified (G:C)$_{75}$ (RGC), biotinylated (G:C)$_{75}$ (RGC-Biotine), poly(I:C) (pIC) or biotinylated poly(I:C) (pIC-Biotine) at the indicated concentrations in the presence (+Tfx) or absence (−Tfx) of the transfection reagent riboxx® FECT (RiboxX GmbH, Radebeul, Germany) according to the manufacturer's instructions. IP-10 was measured in the cell culture supernatant by ELISA. The mean results +/−SEM of two independent experiments are shown. CC: cell culture supernatant as negative control. Tfx: cells incubated with transfection reagent alone.

Figure 21:
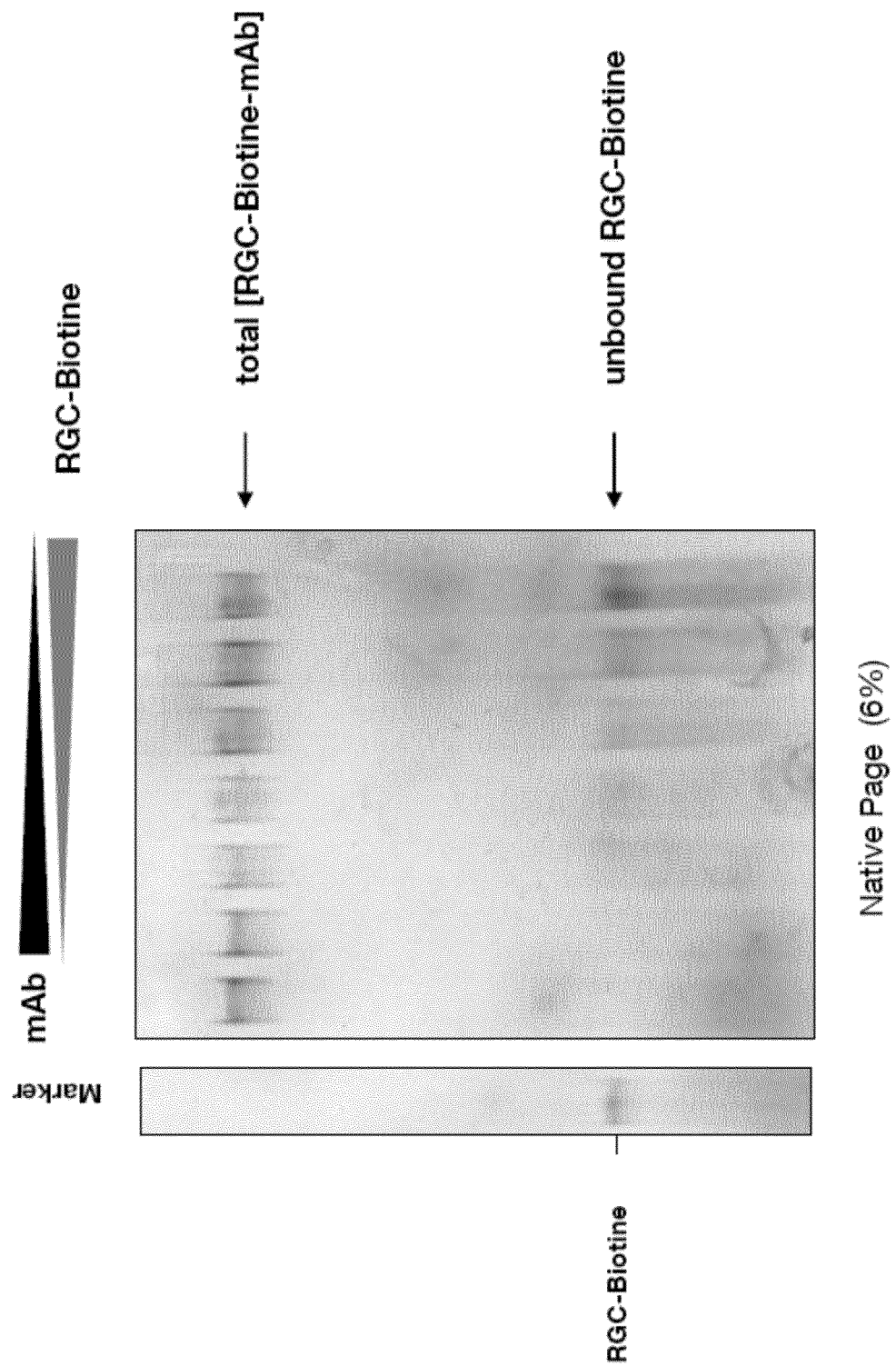

FIG. 21 Analysis of biotinylated (G:C)$_{75}$ bound to anti-biotin antibody (RGC-Biotine-mAb, "ARC") by native polyamide gel electrophoresis (PAGE; 6% polyacrylamide) after staining with ethidium bromide. Biotinylated (G:C)$_{75}$ (RGC-Biotine) was bound to anti-biotin mAb using different ratios of RGC-Biotineto mAB (from left to right (RGC-Biotine:mAb: 1:0.33, 1:0.5, 1:0.67, 1:1, 1.5:1, 2:1, 3:1). The migration of RGC-Biotine alone is shown in the marker lane on the left. The slower migrating RGC-Biotine-mAB construct is clearly visible.

Figure 22:
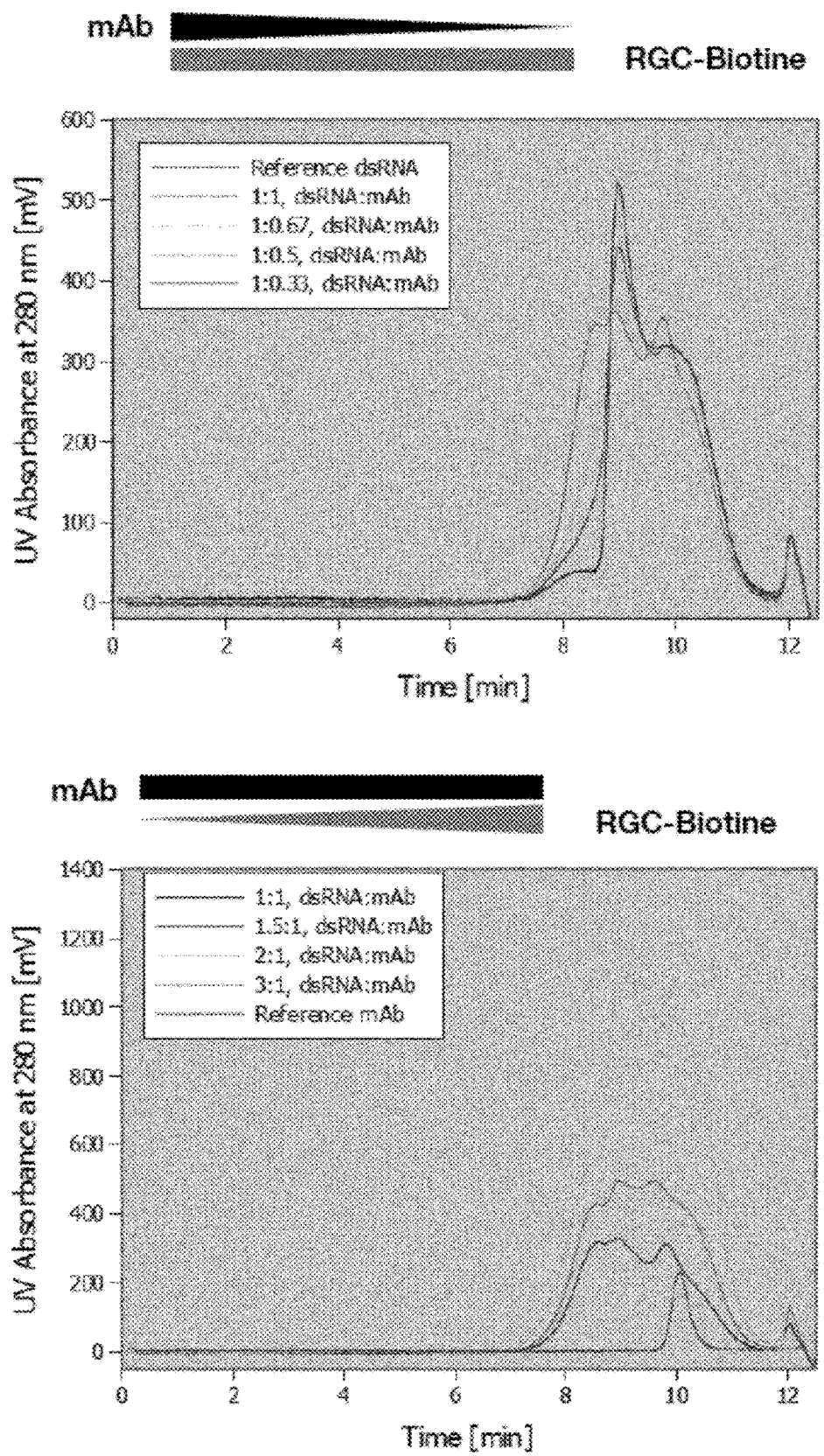

FIG. 22 Analysis of biotinylated (G:C)$_{75}$ bound to anti-biotin antibody (RGC-Biotine-mAb, "ARC") by size-exclusion chromatography (SEC) using HPLC equipment. The constructs of FIG. 25 were subjected to SEC-HPLC in phosphate-buffered saline (PBS; pH 7.4) at a flow rate of 0.45 ml/min with detection by UV radiation at 280 nm. Unmodified (G:C)$_{75}$ and mAb were used as references.

Figure 23:
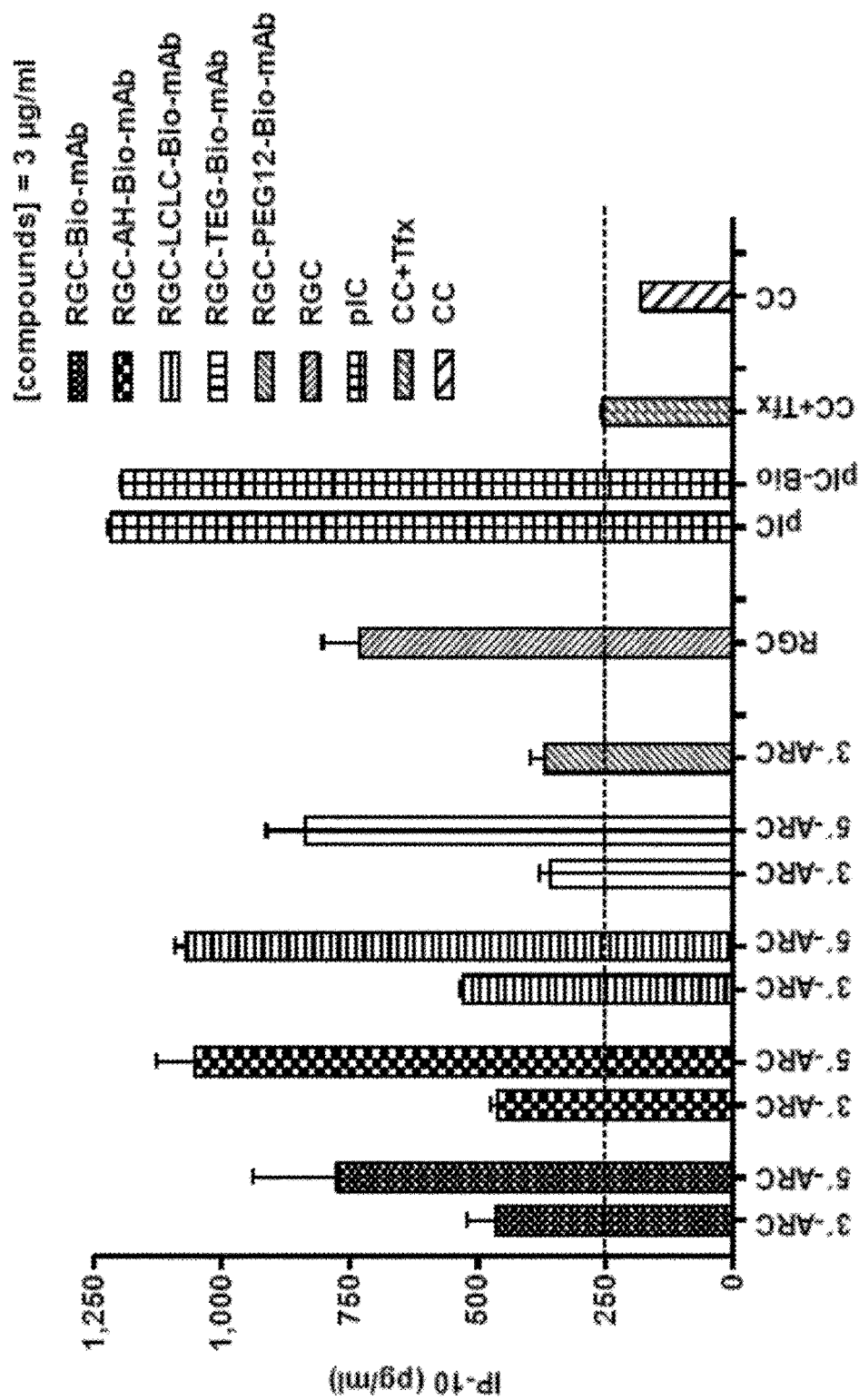

FIG. 23 Activation of HUVECs by various biotinylated (G:C)$_{75}$ coupled to an anti-biotin mAb (ARC constructs). For each type of construct, the modification at the 3' phosphate of the poly(C) strand and the modification at the 5' phosphate of the poly(C) strand were examined. HUVECs were seeded in 24-well plates at $5\times10^4$ cells/well, and incubated with different ARC compounds as indicated at 3 µg/ml in the presence of the transfection reagent riboxx® FECT (RiboxX GmbH, Radebeul, Germany) according to the manufacturer's instructions. IP-10 was measured in the cell culture supernatant by ELISA. The mean results +/−SEM of two independent experiments are shown. CC: cell culture supernatant. CC+Tfx: cells incubated with transfection reagent alone. RGC: unmodified (G:C)$_{75}$. pIC: poly (I:C). pIC-Bio: biotinylated poly(I:C).

Figure 24:
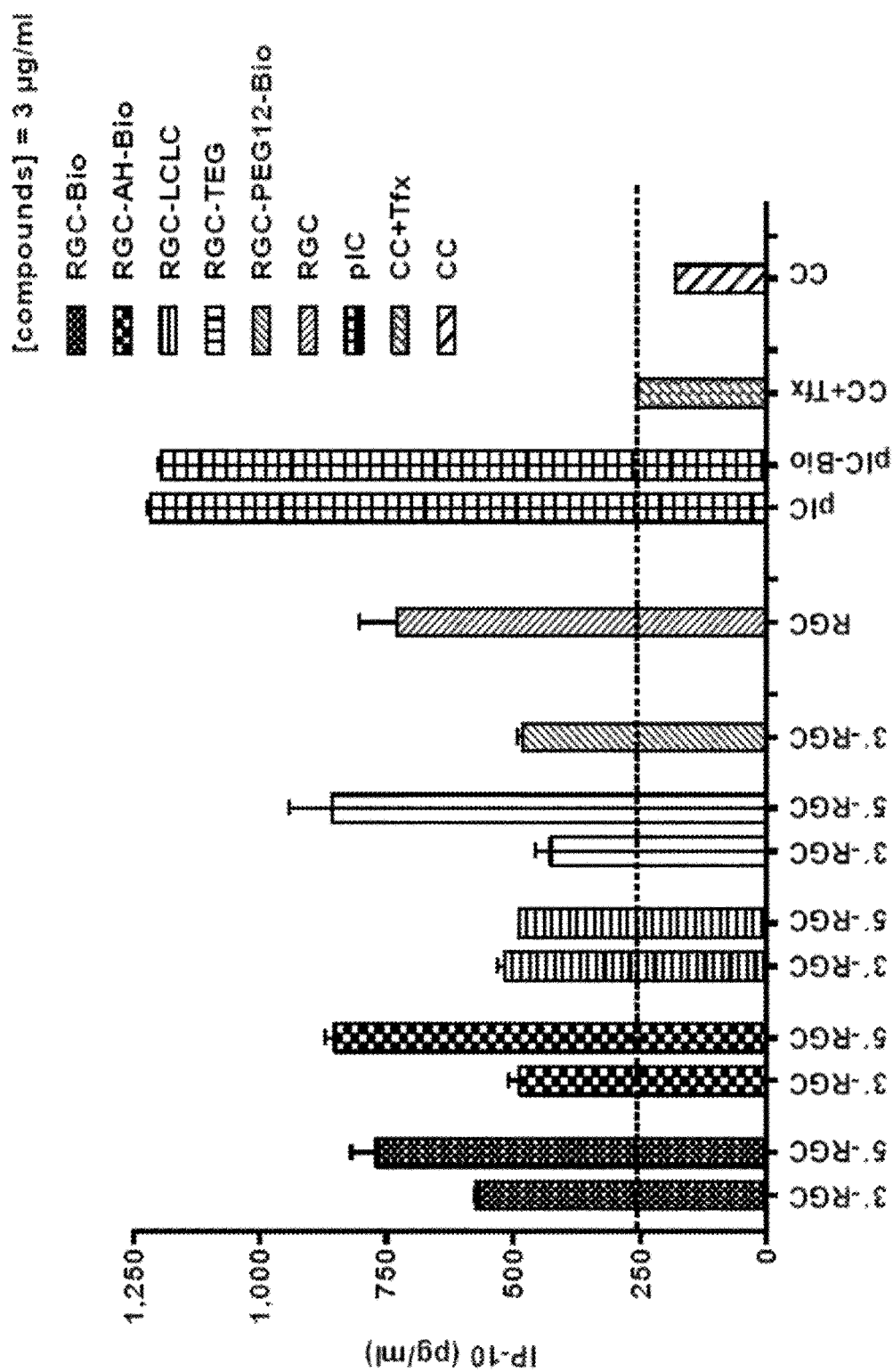

FIG. 24 Activation of HUVECs by various modified (G:C)$_{75}$ constructs wherein the modification is either at a 3'-terminal phosphate or a 5'-terminal phosphate of (G:C)$_{75}$. The same conditions and controls were used as in FIG. 23.

Figure 25:
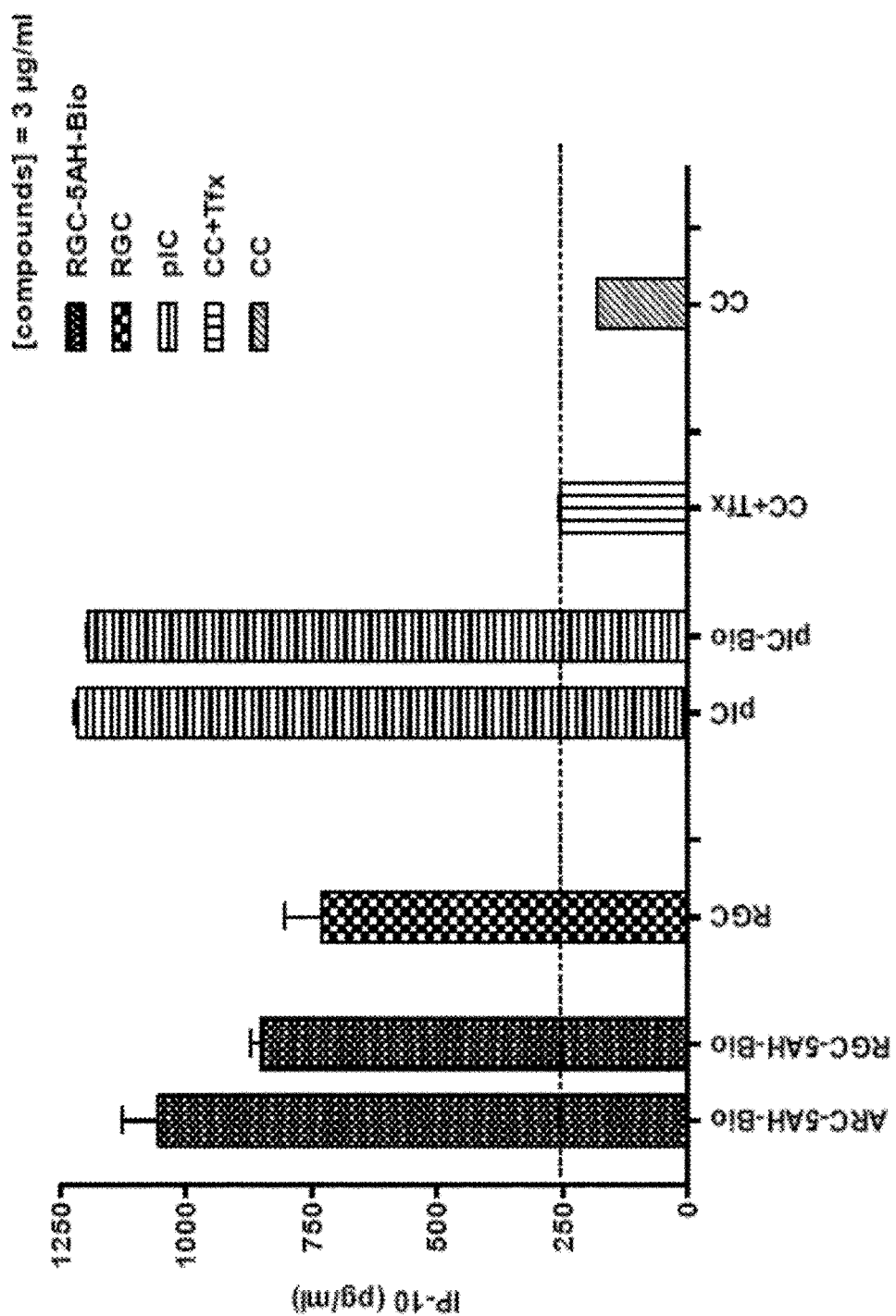

FIG. 25 Activation of HUVECS by biotinylated (G:C)$_{75}$ coupled to mAb (ARC-5AH-Bio) in comparison to biotinylated (G:C)$_{75}$ not coupled to an antibody (RGC-5AH-Bio). The same conditions and controls were used as in FIG. 23.

DETAILED DESCRIPTION OF THE INVENTION

The present invention is further illustrated by the following non-limiting examples:

EXAMPLES

Example 1

Constructs dsRNAs of the present examples were (G:C)$_x$ with x being 75 or 100, respectively. In the following, all references to (G:C)x constructs are understood to be poly(rG:rC) molecules of the indicated length, i.e. dsRNAs. The poly(C) strand was prepared by chemical synthesis, and either the 5'-terminal phosphate or the 3'-terminal phosphate was derivatized using standard nucleic acid modification chemistry (see, e.g. Hermanson G. T. (2008), supra, so as to provide 3'-terminal or 5'-terminal structures, in particular those according to formulas (II) to (VIII).

The complementary poly(G) strand was prepared using a RNA-dependent RNA polymerase from a calicivirus, rGTP, and appropriate buffer conditions as outlined in WO-A-2007/012329, with the modified (for controls: unmodified) poly(C) strand as the template. The usage of the viral RdRp leads to a free triphosphate group at the 5'-terminal end of the poly(G) strand.

In further embodiments, constructs having a biotin moiety (see formula (III), (VI) and (VIII) to (XI), respectively) were coupled to an anti-biotin mAb (Sigma). Analytics of exemplary antibody-coupled constructs is shown in FIGS. 21 (native PAGE) and 22 (SEC-HPLC).

The following modified dsRNA constructs were prepared:

RGC75-3AH: $(G:C)_{75}$ having structure according to formula (II) at 3'-terminal phosphate of the poly(C) strand RGC75-5AH-Bio: $(G:C)_{75}$ having structure according to formula (VI) at 5'-terminal phosphate of the poly(C) strand RGC100-3AH-Bio: $(G:C)_{100}$ having structure according to formula (III) at 3'-terminal phosphate of the poly(C) strand RGC100-3AH-Bio-mAb: $(G:C)_{100}$ having structure according to formula (III) at 3'-terminal phosphate of the poly(C) strand wherein the biotin moiety is bound to an anti-biotin mAb.

RGC-Biotine: $(G:C)_{75}$ having structure according to formula (III) at 3'-terminal phosphate of the poly(C) strand or having the structure according to formula (V) at 5'-terminal phosphate of the poly(C) strand RGC-Bio: same as RGC-Biotine but having a methyl amido-biotin group coupled to the 3' or 5' teriminal phosphate instead of a hexyl amido-biotin group.

RGC-Bio-mAb: RGC-Bio conjugated to anti-biotin mAb

RGC-LCLC: $(G:C)_{75}$ having structure according to formula (IX) at 3'-terminal phosphate (R in formula (IX)=$CH_2OH$) of the poly(C) strand or having the structure according to formula (IX) at 5'-terminal phosphate (R in formula (IX)=H) of the poly(C) strand RGC-LCLC-Bio-mAb: RGC-LCLC conjugated to anti-biotin mAb RGC-TEG: $(G:C)_{75}$ having structure according to formula (X) at 3'-terminal phosphate (R in formula (IX)=$CH_2OH$) of the poly(C) strand or having the structure according to formula (X) at 5'-terminal phosphate (R in formula (IX)=H) of the poly(C) strand RGC-TEG-Bio-mAb: RGC-TEG conjugated to anti-biotin mAb RGC-PEG12-Bio: $(G:C)_{75}$ having structure according to formula (XI) at 3'-terminal phosphate (R in formula (IX)=$CH_2OH$) of the poly(C) strand or having the structure according to formula (XI) at 5'-terminal phosphate (R in formula (IX)=H) of the poly(C) strand RGC-PEG12-Bio-mAB: RGC-PEG12-Bio conjugated to anti-biotin mAb RGC-5AH-Bio: Same as RGC75-5AH-Bio ARC-5AH-Bio: RGC-5AH-Bio conjugated to anti-biotin mAb Example 2

Activation of Cultured Immune and Non-immune Cells with dsRNA Constructs According to the Invention Cells (HUVEC endothelial cells, JAWS II dendritic cells or RAW 264.7 macrophages) were cultured in 24-well plates at a density of $5 \times 10^4$ cells/well in RPMI-1640 medium plus 10% human AB serum (CCPRO, Neustadt, Germany). Cells were incubated with the respective dsRNA construct and at the concentration(s) shown in the Figs. and/or as described in the above FIG. legends, respectively, for 24 to 72 hours in the presence of riboxx® FECT (RiboxX GmbH, Radebeul, Germany) according to the manufacturers instructions. Secretion of cytokines (IL-6) or chemokines (IP-10, MCP-1, RANTES, I-TAC and/or GRO-α) was measured using ELISA testing for the respective molecule.

Example 3

Cellular Localization of dsRNA Constructs $(G:C)_{75}$ was labelled with Atto488 (ATTO-TEC GmbH, Siegen, Germany) according to the manufacturer's instructions (construct RGC-Atto488). HUVECs were cultured and transfected with RGC-Attto488 as outlined in Example 2. In further experiments, cells were stained with FITC-labelled anti-TLR-3, FITC-labelled anti-EEA-1 or FITC-labelled anti-LAMP-1. Analysis was carried by confocal microscopy.

Example 4

Expression of TLR-3, E-Selectin and Integrins by HUVECs After Stimulation with dsRNA Construct HUVECs were transfected with $(G:C)_{75}$ dsRNA at 6 µg/ml according to the protocol of Example 2. Expression of proteins of interest was analyzed by cell cytometry on a CUBE machine (PartecGmbH, Meckenheim, Germany) as outlined in the legend of FIG. 21.

The experiments as further described in the Figs. and the above FIG. legends show that dsRNA constructs of the invention strongly activate immune (JAWS II dendritic cells, RAW 254.7 macrophages) as well as non-immune cells (HUVEC endothelial cells); see FIGS. 3, 4, 5, 6, 8, 9, 10, 19, 20, 23, 24, 25). Thus, the modification of dsRNAs according to the present invention does not impede the activation of immune and non-immune cells seen with unmodified dsRNA constructs. The activation by dsRNA constructs of the invention can be as high as that of the reference substance poly(I:C). Moreover, even the coupling of larger carrier molecules such as a monoclonal antibody does not interfere with the TLR-3 and RLR, in particular RIG-I, activating properties of the constructs according to the invention (see FIG. 23), but the activation is even higher with the mAb-conjugated compared to the same construct non conjugated to the mAb (compare the results of FIG. 23 with those of FIG. 24; see also FIG. 25). With respect to mAb-conjugated constructs it is preferable to have the modification at a 5'-terminal phosphate in order to achieve optimal activation at least in the case of endothelial cells (HUVECs); cf. FIG. 23.

Localization studies (cf. FIGS. 11 to 15) show that dsRNA compounds according to the invention are taken up by endothelial cells (HUVECs) and localized to the endosome and lysosomes, leading to activation of endosomal TLR-3. This activation leads to a very high level of chemokine secretion such as IP-10 (=CXCL10) and I-TAC (=CXCL11) but not pro-inflammatory cytokines such as TNF-α or IL-6. IP-10 is an important trigger of integrin and selectin expression and plays an important role in T cell recruitment. IP-10 has also strong ant-angiogenic properties such that dsRNA constructs of the invention are particularly suited for cancer treatment (by impeding or hindering of tumoral neo-angiogenesis). Other chemokines secreted by HUVECs upon treatment with dsRNA constructs of the invention, such as RANTES (=CCL5), MCP-1 (=CCL2) and GRO-α (=CXCL1) play major roles in T cell and leucocyte/ neutrophil recruitment further underscoring the potential of the dsRNA constructs of the invention for cancer and/or tumor treatment.

Figure 2:
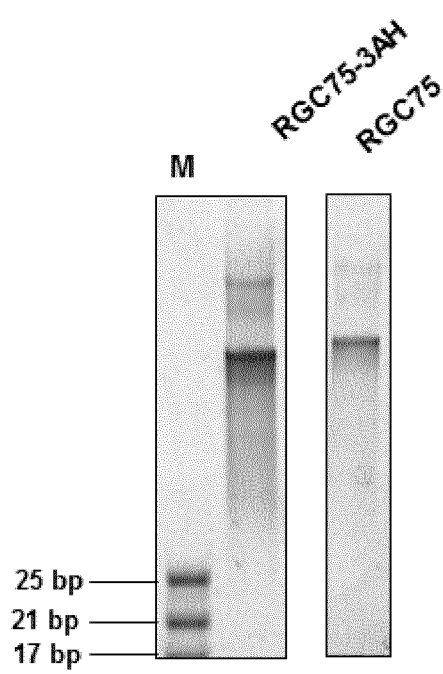
FIG. 2 Analytics of RGC75 compounds as shown in FIG. 1. Compounds were analyzed by LC/ESI-MS, as well as HPLC and PAGE. A representative example of PAGE analysis is shown. M, Molecular Weight Marker (dsRNA)
Figure 3:
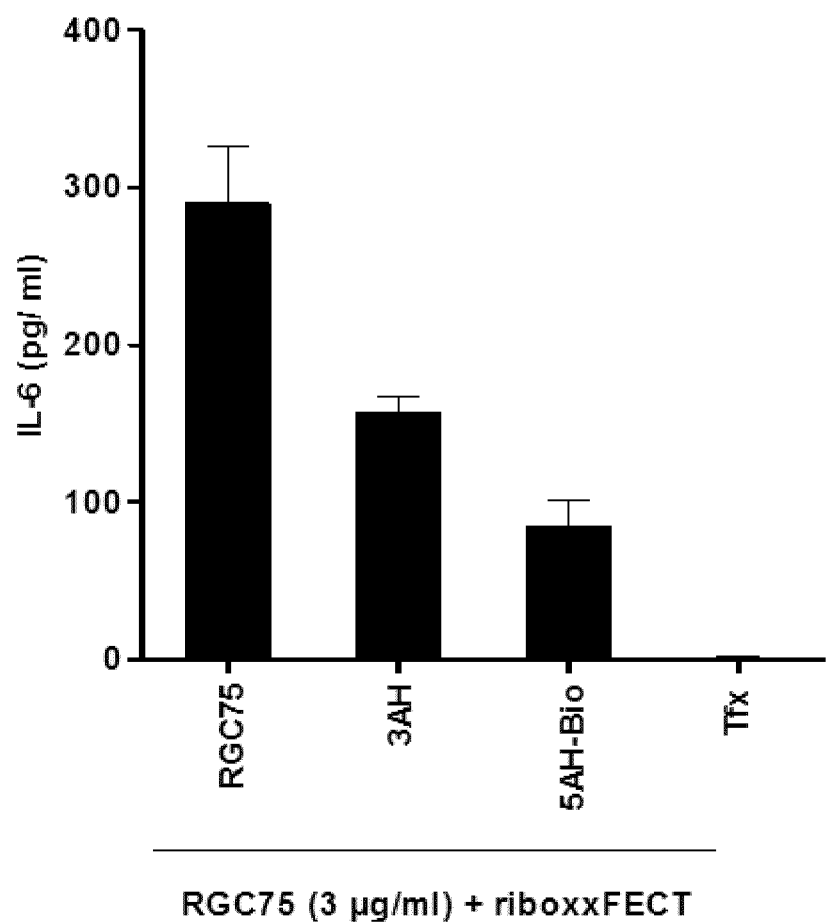
FIG. 3: Activation of HUVECs by RGC75 constructs as outlined in FIG. 5 upon transfection. HUVECs were seeded in 24-well plates at $5 \times 10^4$ cells/well, and incubated with RGC75 compounds (as outlined in FIG. 1) at 3 µg/ml in the presence of transfection reagent (Tfx) riboxx® FECT (RiboxX GmbH, Radebeul, Germany) according to the manufacturer's instructions. Mean +/−SEM of two independent measurements is shown. CC: cell culture; Tfx: cells with transfection reagent alone. IL-6 was measured in the supernatant by ELISA.
Figure 4:
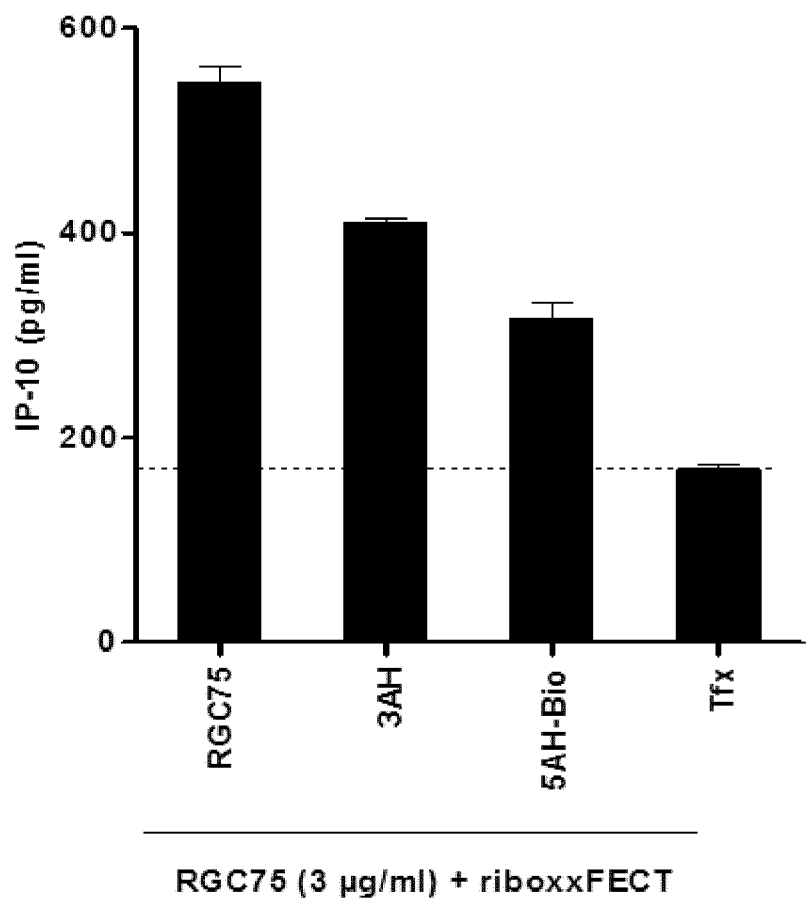
FIG. 4: Activation of HUVECs by RGC75 constructs as outlined in FIG. 1 upon transfection. HUVECs were seeded in 24-well plates at $5 \times 10^4$ cells/well, and incubated with RGC75 compounds (as outlined in FIG. 1) at 3 µg/ml in the presence of transfection reagent (Tfx) riboxx® FECT (RiboxX GmbH, Radebeul, Germany) according to the manufacturer's instructions. Mean +/−SEM of two independent measurements is shown. CC: cell culture; Tfx: cells with transfection reagent alone. IP-10 was measured in the supernatant by ELISA.
Figure 5:
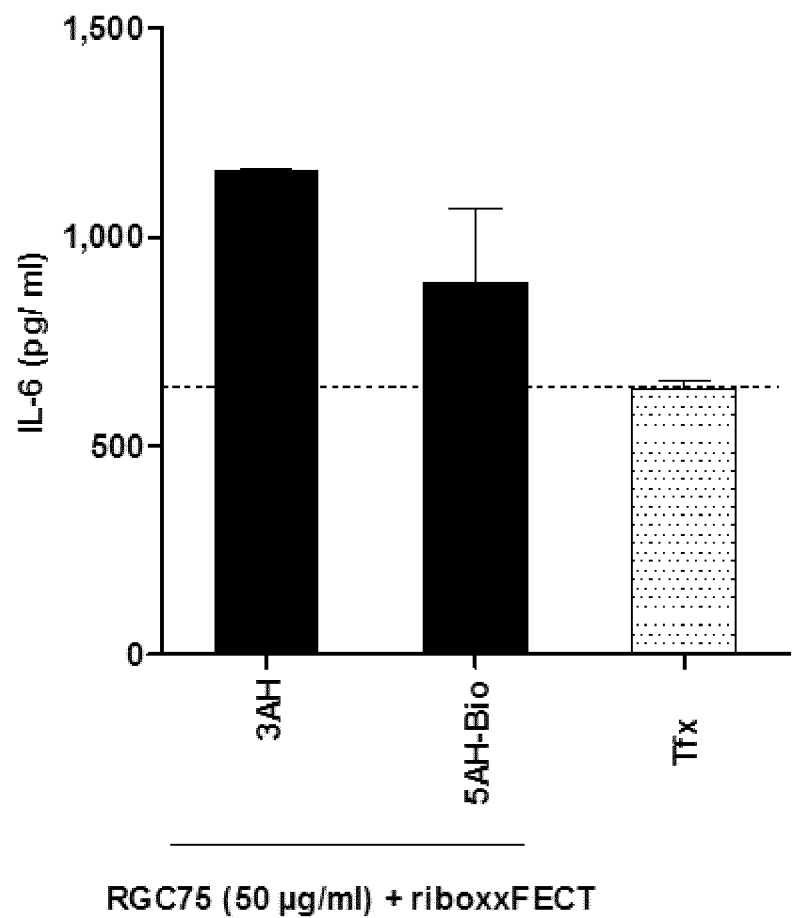
FIG. 5: Activation of JAWS II dendritic cells by RGC75 constructs as outlined in FIG. 1 upon transfection. JAWS II dendritic cells were seeded in 96-well plates at $5 \times 10^4$ cells/well, and incubated with RGC75 compounds (as outlined in FIG. 1) at 50 µg/ml in the presence of transfection reagent (Tfx) riboxx® FECT (RiboxX GmbH, Radebeul, Germany) according to the manufacturer's instructions. Mean +/−SEM of two independent measurements is shown. CC: cell culture; Tfx: cells with transfection reagent alone. IL-6 was measured in the supernatant by ELISA.
Figure 6:
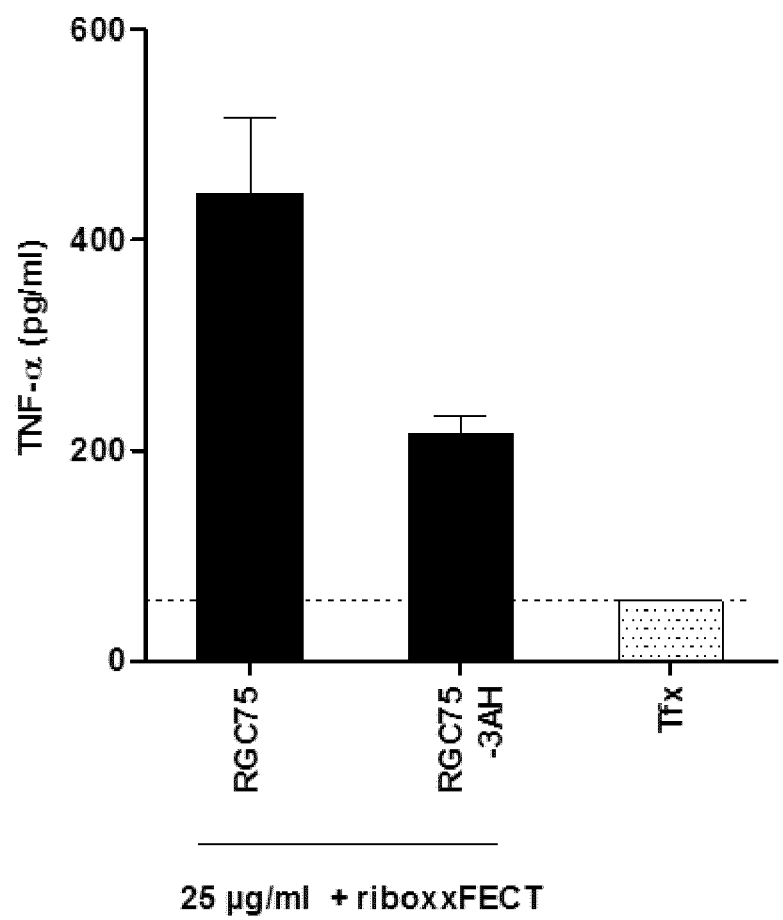
FIG. 6: Activation of RAW 264.7 macrophages by RGC75 constructs as outlined in FIG. 1 upon transfection. RAW 264.7 macrophages were seeded in 96-well plates at $5 \times 10^4$ cells/well, and incubated with RGC75 compounds (as outlined in FIG. 1) at 25 µg/ml in the presence of transfection reagent (Tfx) riboxx® FECT (RiboxX GmbH, Radebeul, Germany) according to the manufacturer's instructions. Mean +/−SEM of two independent measurements is shown. CC: cell culture; Tfx: cells with transfection reagent alone. TNF-α was measured in the supernatant by ELISA.
Figure 8:
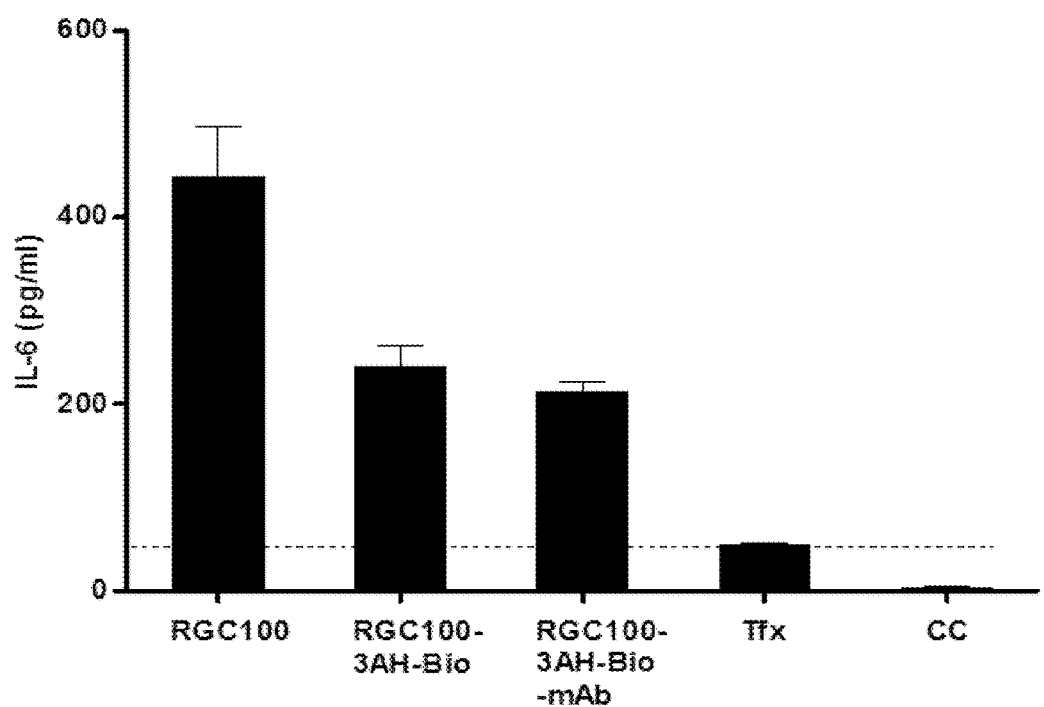
FIG. 8 Activation of HUVECs by RGC100 constructs as outlined in FIG. 7 upon transfection. HUVECs were seeded in 24-well plates at $5 \times 10^4$ cells/well, and incubated with RGC100 compounds (as outlined in FIG. 7) for 16 h at 3 µg/ml in the presence of transfection reagent (Tfx) riboxx® FECT (RiboxX GmbH, Radebeul, Germany) according to the manufacturer's instructions. Mean +/−SEM of two independent measurements is shown. CC: cell culture; Tfx: cells with transfection reagent alone. IL-6 was measured in the supernatant by ELISA.
Figure 9:
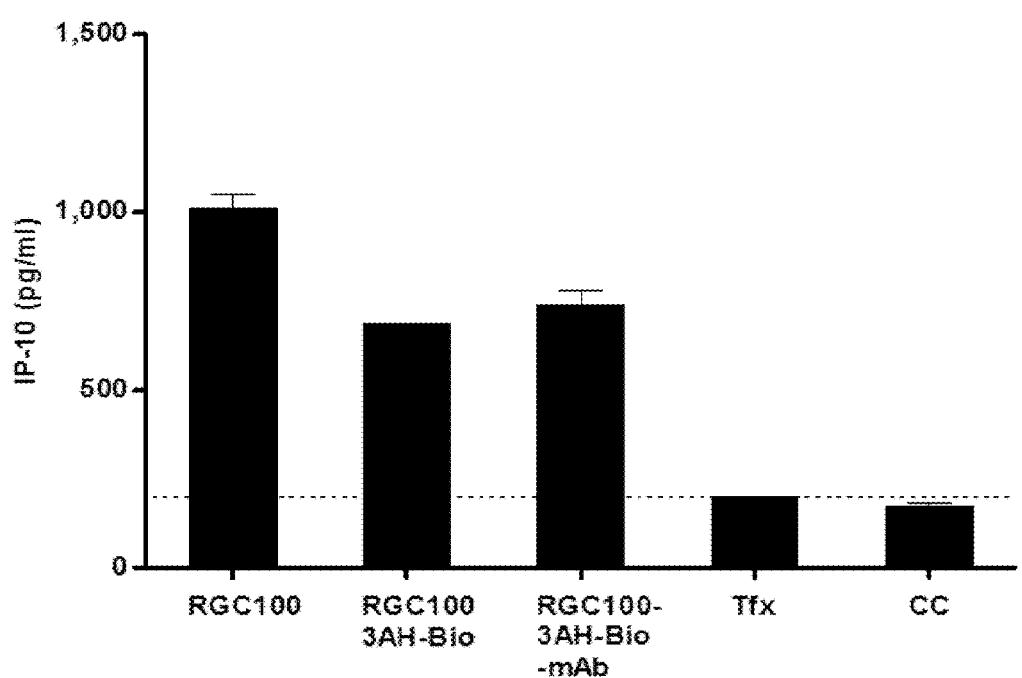
FIG. 9: Activation of HUVECs by RGC100 constructs as outlined in FIG. 7 upon transfection. HUVECs were seeded in 24-well plates at $5 \times 10^4$ cells/well, and incubated with RGC100 compounds (as outlined in FIG. 7) for 16 h at 3 µg/ml in the presence of transfection reagent (Tfx) riboxx® FECT (RiboxX GmbH, Radebeul, Germany) according to the manufacturer's instructions. Mean +/−SEM of two independent measurements is shown. CC: cell culture; Tfx: cells with transfection reagent alone. IP-10 was measured in the supernatant by ELISA.
Figure 10:
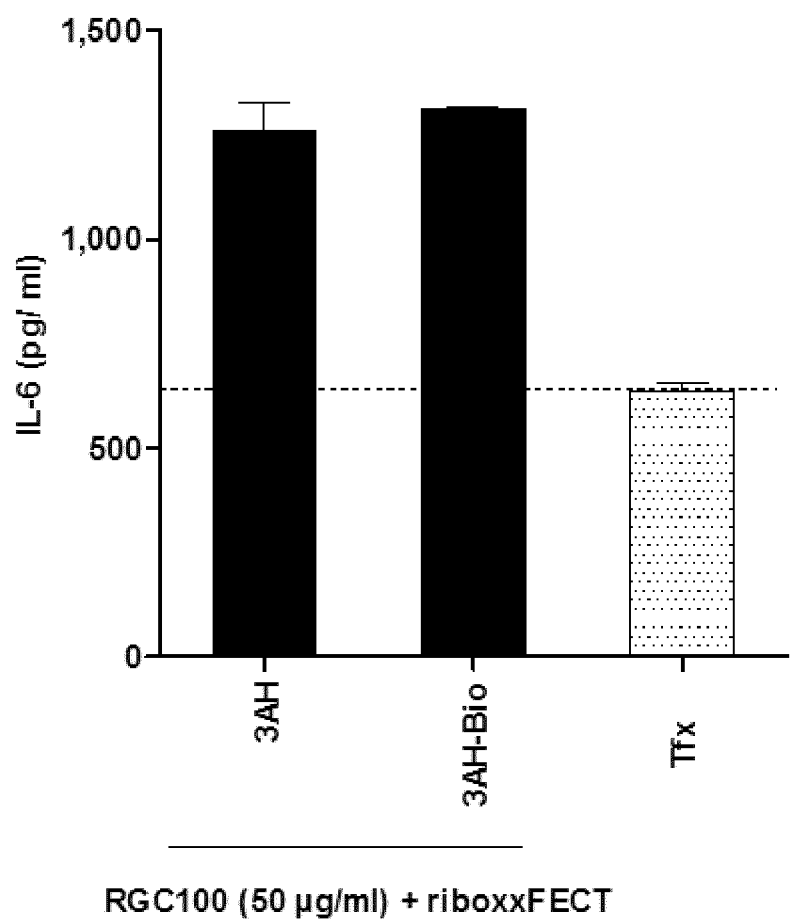
FIG. 10: Activation of JAWS II dendritic cells by RGC100 constructs as outlined in FIG. 7 upon transfection. JAWS II DCs were seeded in 24-well plates at $5 \times 10^4$ cells/well, and incubated with RGC100 compounds (as outlined in FIG. 7) at 50 µg/ml in the presence of transfection reagent (Tfx) riboxx® FECT (RiboxX GmbH, Radebeul, Germany) according to the manufacturer's instructions. Mean +/−SEM of two independent measurements is shown. CC: cell culture; Tfx: cells with transfection reagent alone. IL-6 was measured in the supernatant by ELISA.
Figure 11:
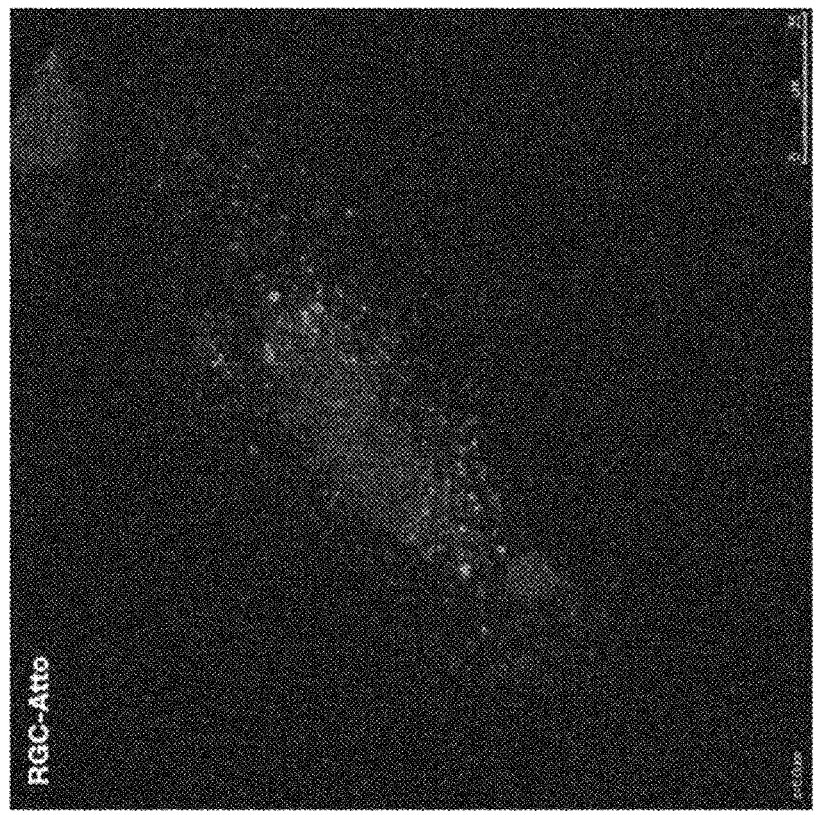
FIG. 11 Localization of dsRNA constructs in HUVECs. HUVECs were seeded in 24-well plates at $5 \times 10^4$ cells/well, and incubated with labelled $(G:C)_{75}$ RNA (RGC-Atto488) at 25 µg/ml in the presence of the transfection reagent (Tfx) riboxx® FECT (RiboxX GmbH, Radebeul, Germany) according to the manufacturer's instructions. The cells were analyzed by confocal microscopy.
Figure 11:
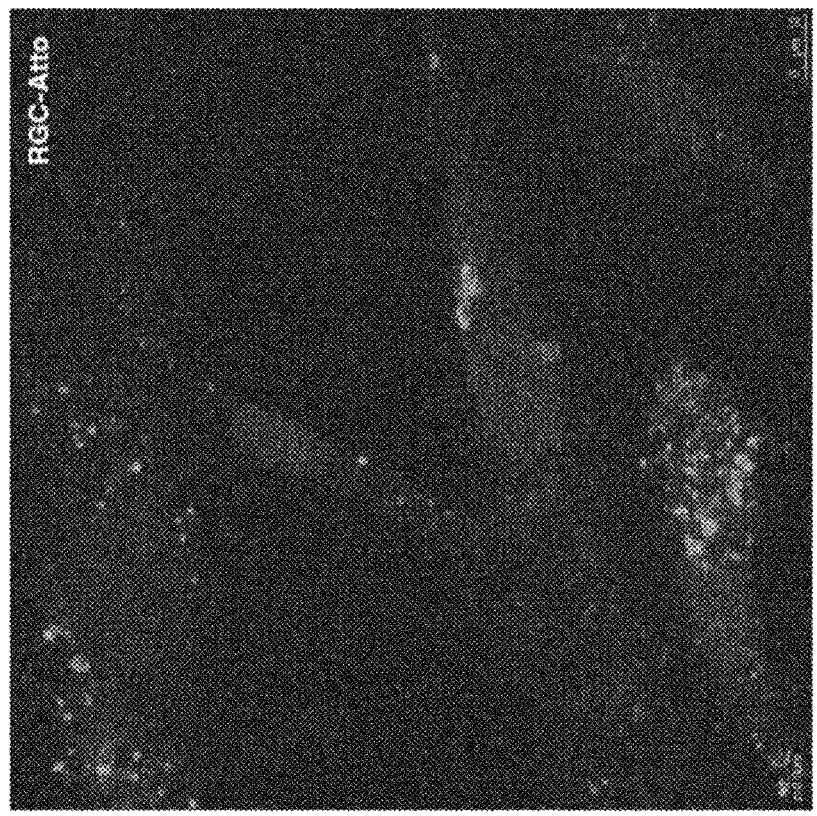
Figure 12:
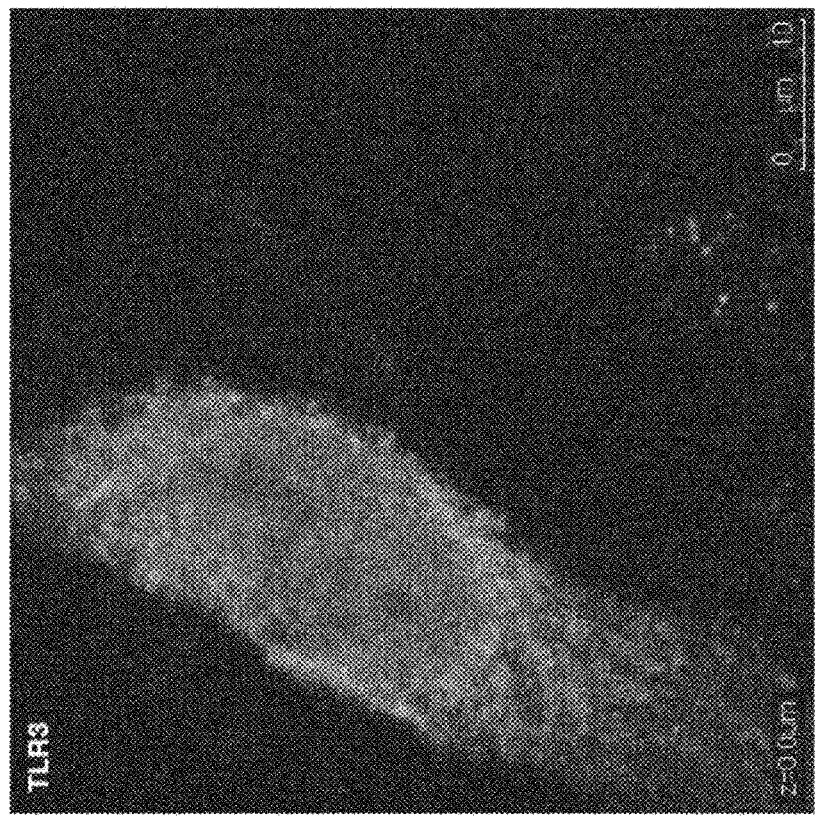
FIG. 12 Expression of TLR-3 in HUVECs. HUVECs were seeded in 24-well plates at $5 \times 10^4$ cells/well, stained with anti-TLR-3-FITC antibody and analyzed by confocal microscopy.
Figure 12:
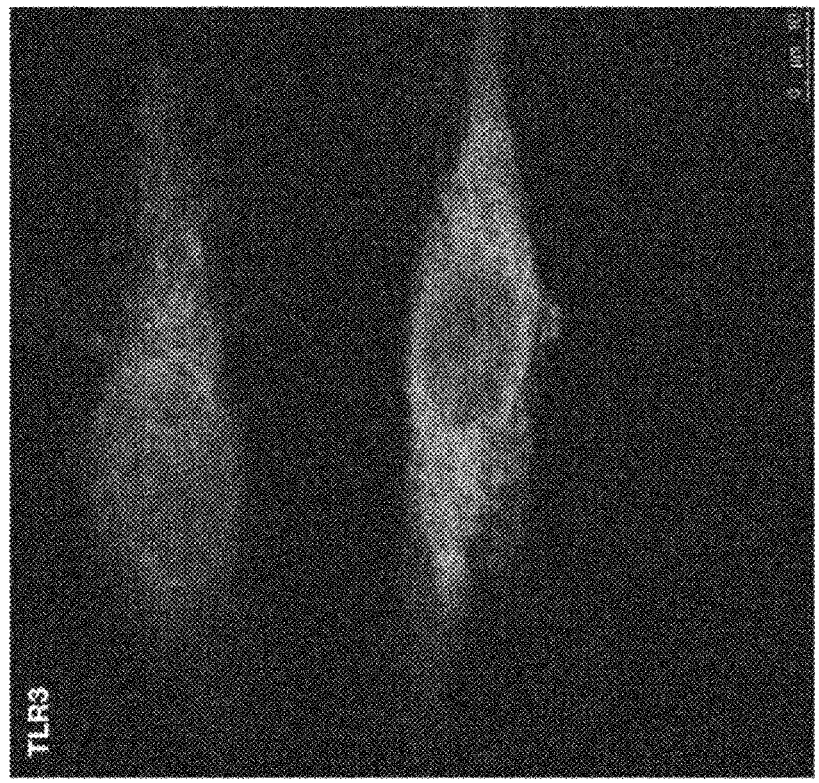
Figure 13:
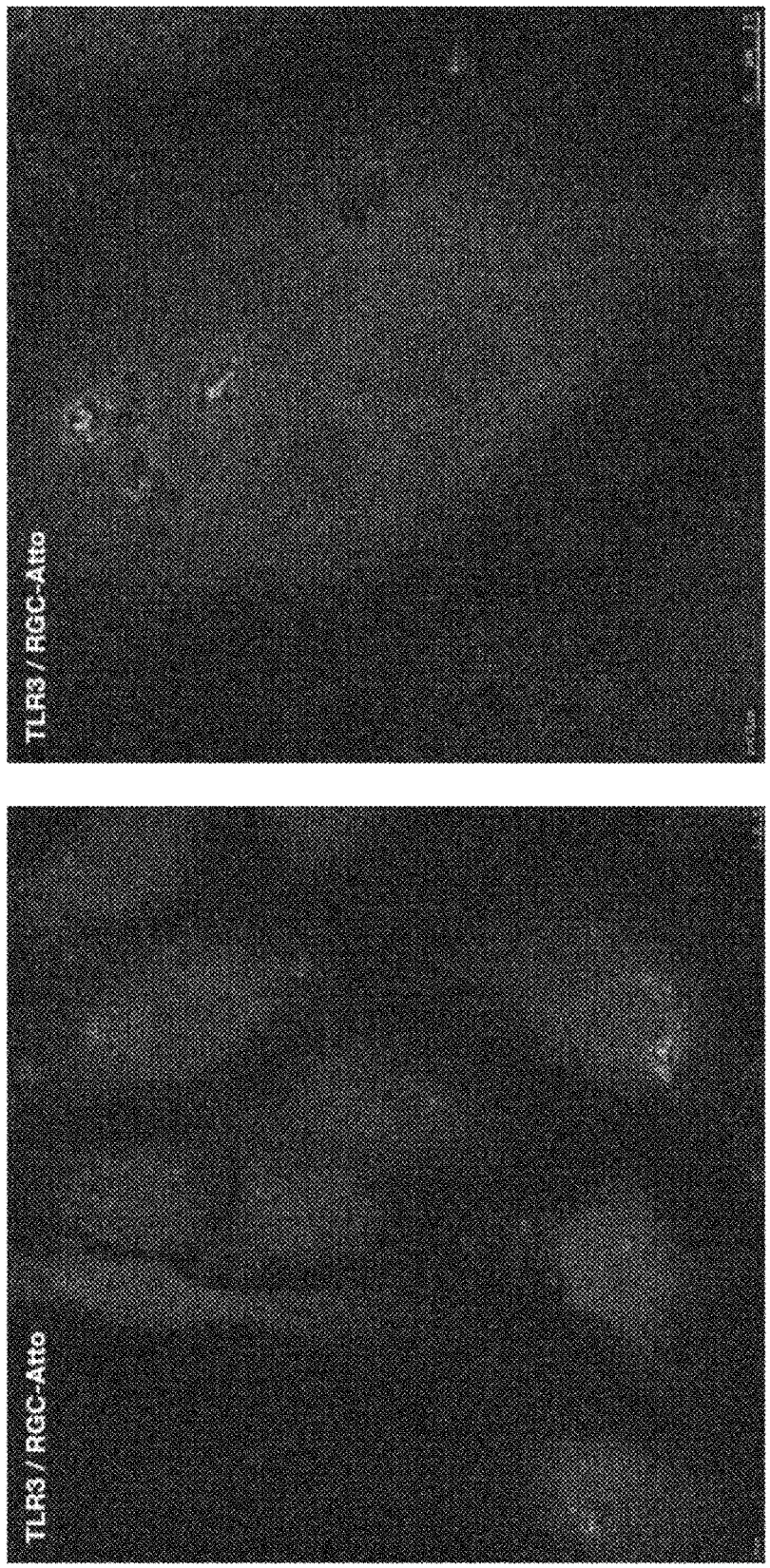
FIG. 13 Localization of dsRNA constructs in HUVECs. HUVECs were seeded in 24-well plates at $5 \times 10^4$ cells/well, and incubated with labelled $(G:C)_{75}$ RNA (RGC-Atto488) at 25 µg/ml in the presence of the transfection reagent (Tfx) riboxx® FECT (RiboxX GmbH, Radebeul, Germany) according to the manufacturer's instructions. The cells were stained with anti-TLR-3-FITC and analyzed by confocal microscopy.
Figure 14:
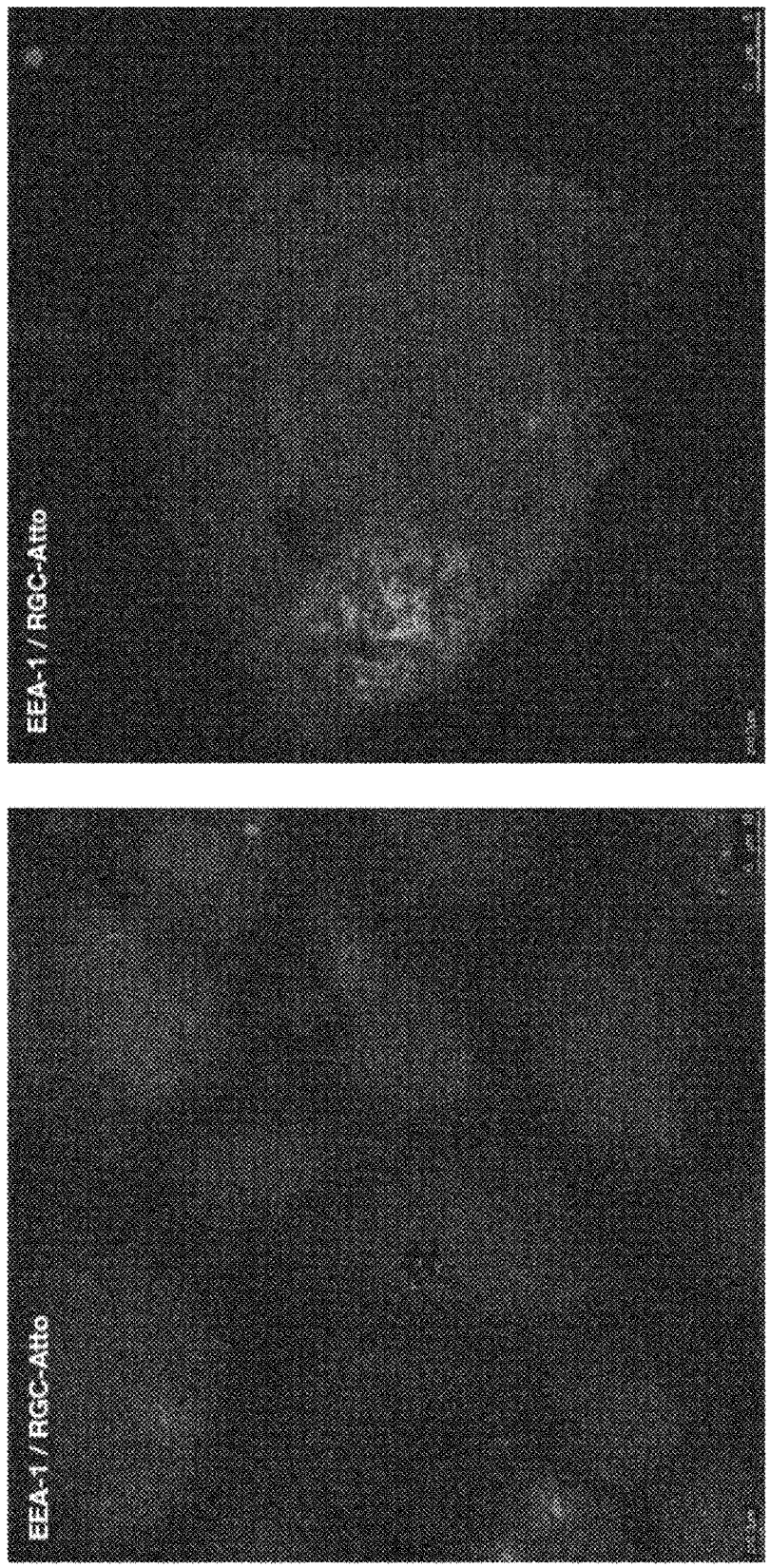
FIG. 14 Localization of dsRNA constructs in HUVECs. HUVECs were seeded in 24-well plates at $5 \times 10^4$ cells/well, and incubated with labelled $(G:C)_{75}$ RNA (RGC-Atto488) at 25 µg/ml in the presence of the transfection reagent (Tfx) riboxx® FECT (RiboxX GmbH, Radebeul, Germany) according to the manufacturer's instructions. The cells were stained with anti-EEA-1-FITC antibody and analyzed by confocal microscopy.
Figure 15:
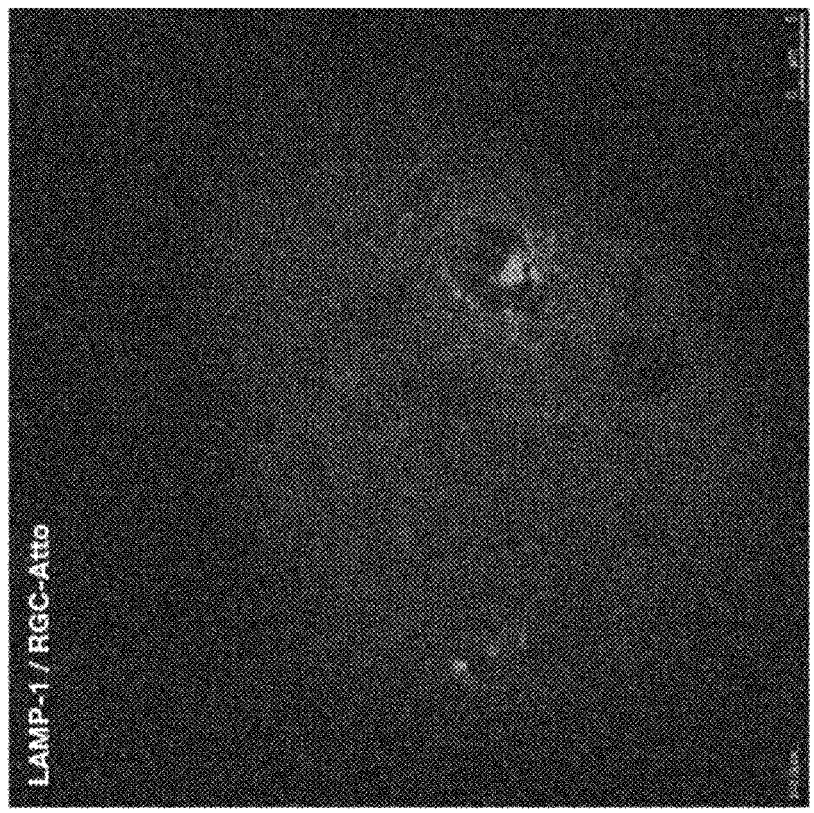
FIG. 15 Localization of dsRNA constructs in HUVECs. HUVECs were seeded in 24-well plates at $5 \times 10^4$ cells/well, and incubated with labelled $(G:C)_{75}$ RNA (RGC-Atto488) at 25 µg/ml in the presence of the transfection reagent (Tfx) riboxx® FECT (RiboxX GmbH, Radebeul, Germany) according to the manufacturer's instructions. The cells were stained with anti-LAMP-1-FITC antibody and analyzed by confocal microscopy.
Figure 15:
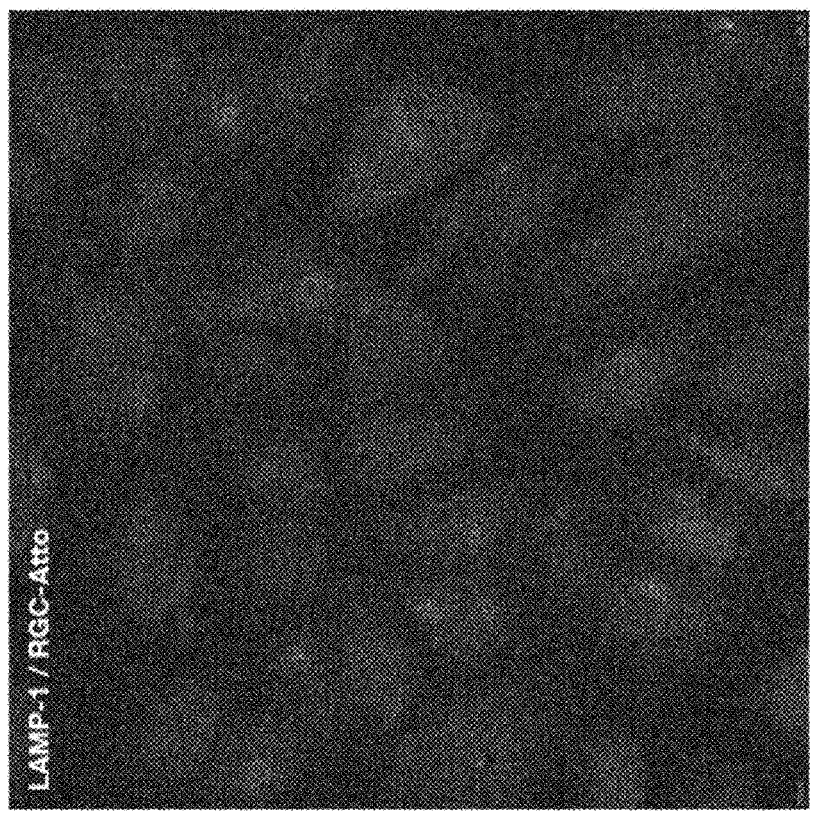
Figure 16:
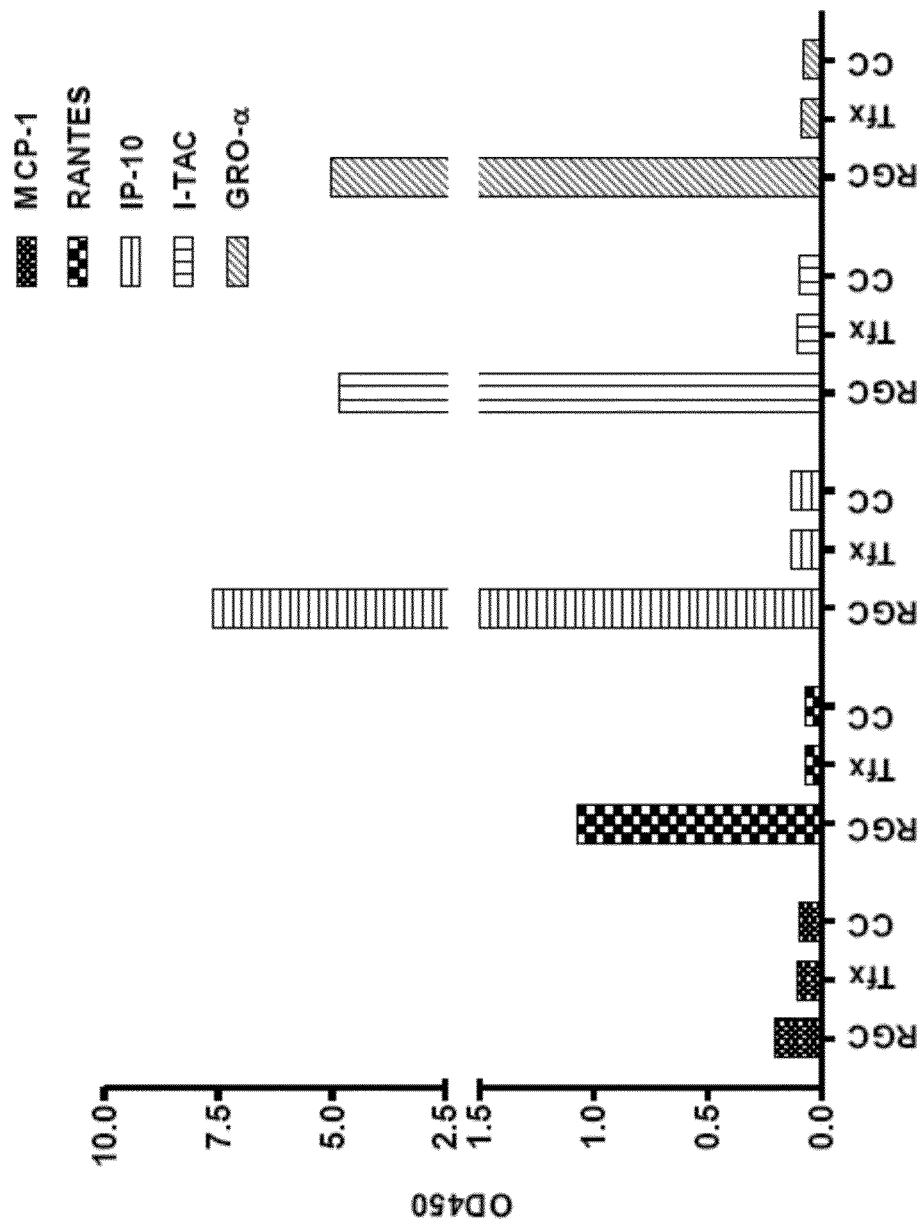
FIG. 16 HUVECs secrete various chemokines upon transfection with $(G:C)_{75}$ RNA. HUVECs were seeded in 24-well plates at $5 \times 10^4$ cells/well, and incubated with $(G:C)_{75}$ RNA (RGC) at 6 µg/ml in the presence of the transfection reagent (Tfx) riboxx® FECT (RiboxX GmbH, Radebeul, Germany) according to the manufacturer's instructions. The mean results of two independent measurements for each cytokine are shown. CC: cell culture supernatant as negative control.
Figure 17A:
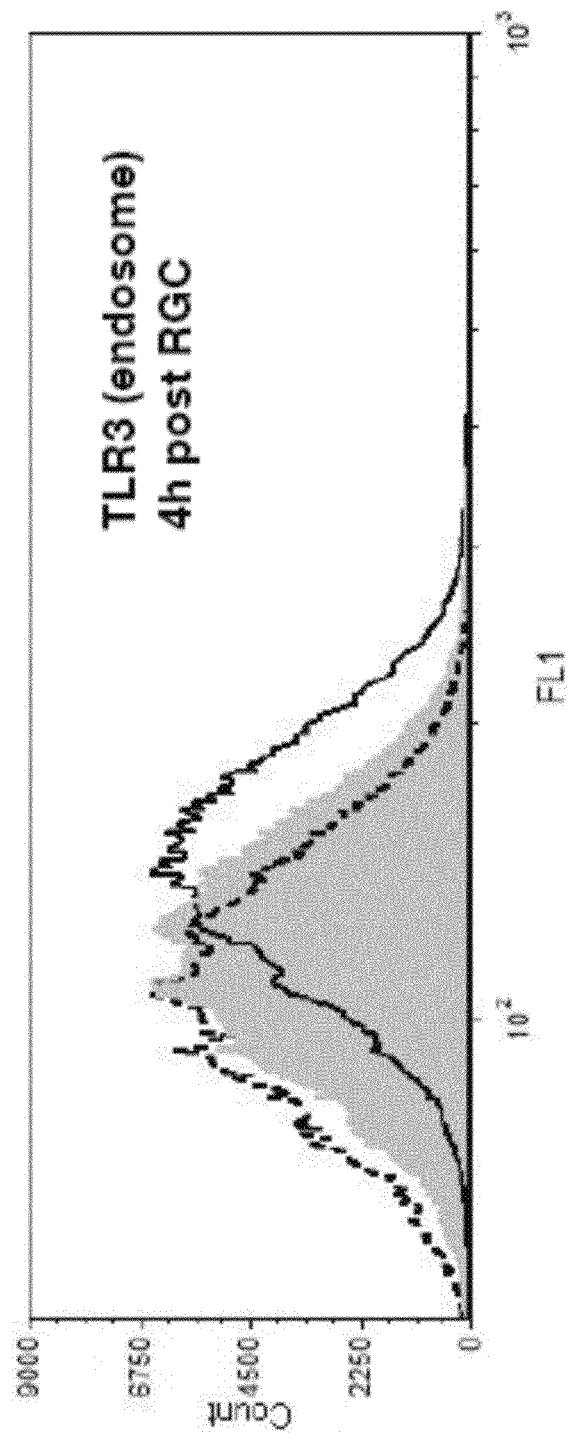
Figure 17B:
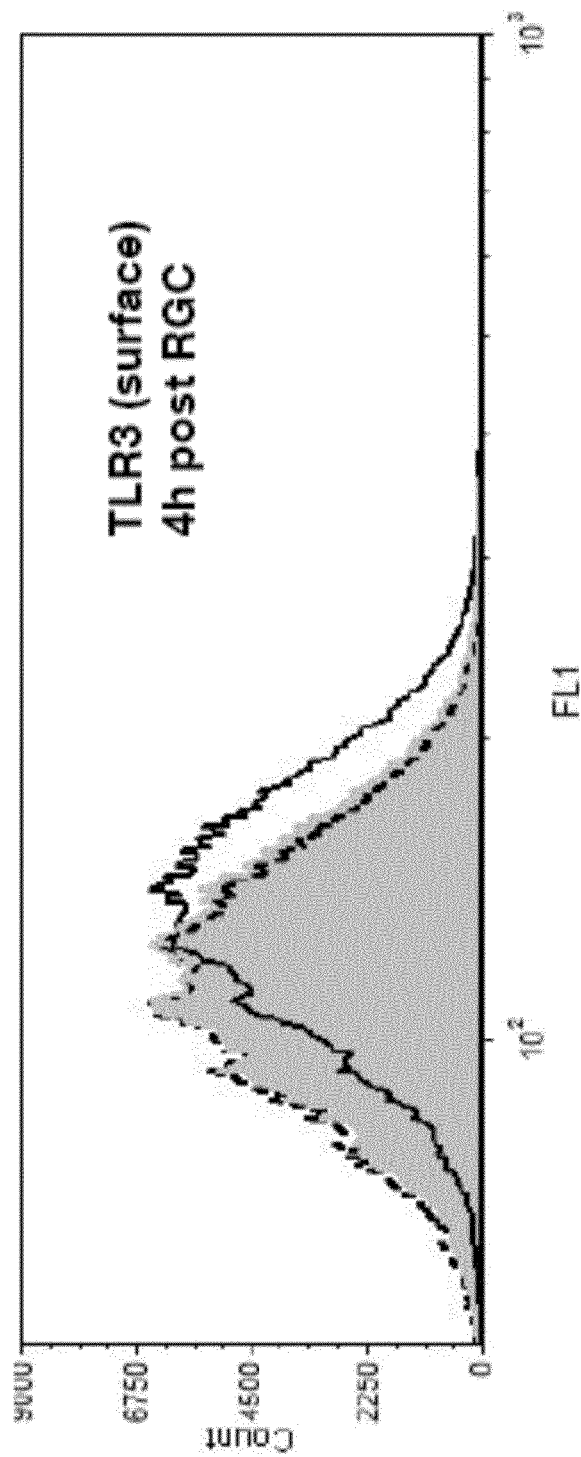
Figure 17C:
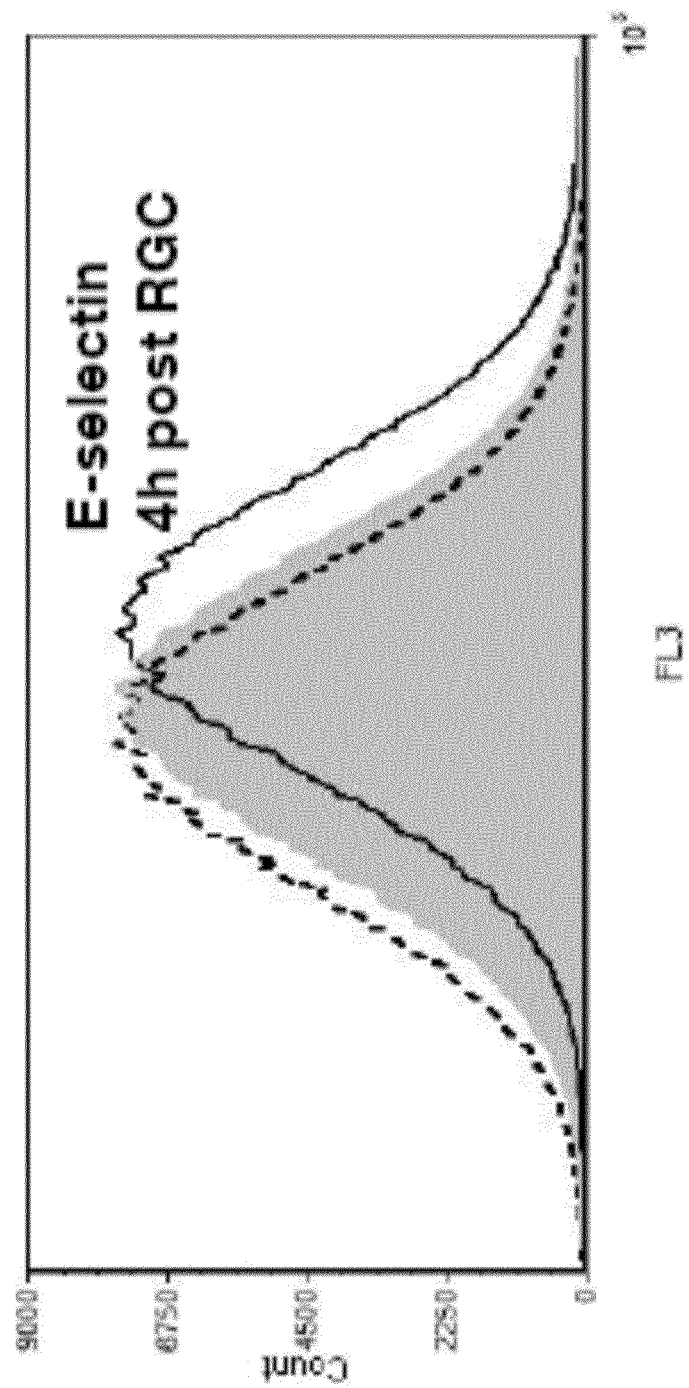
Figure 17D:
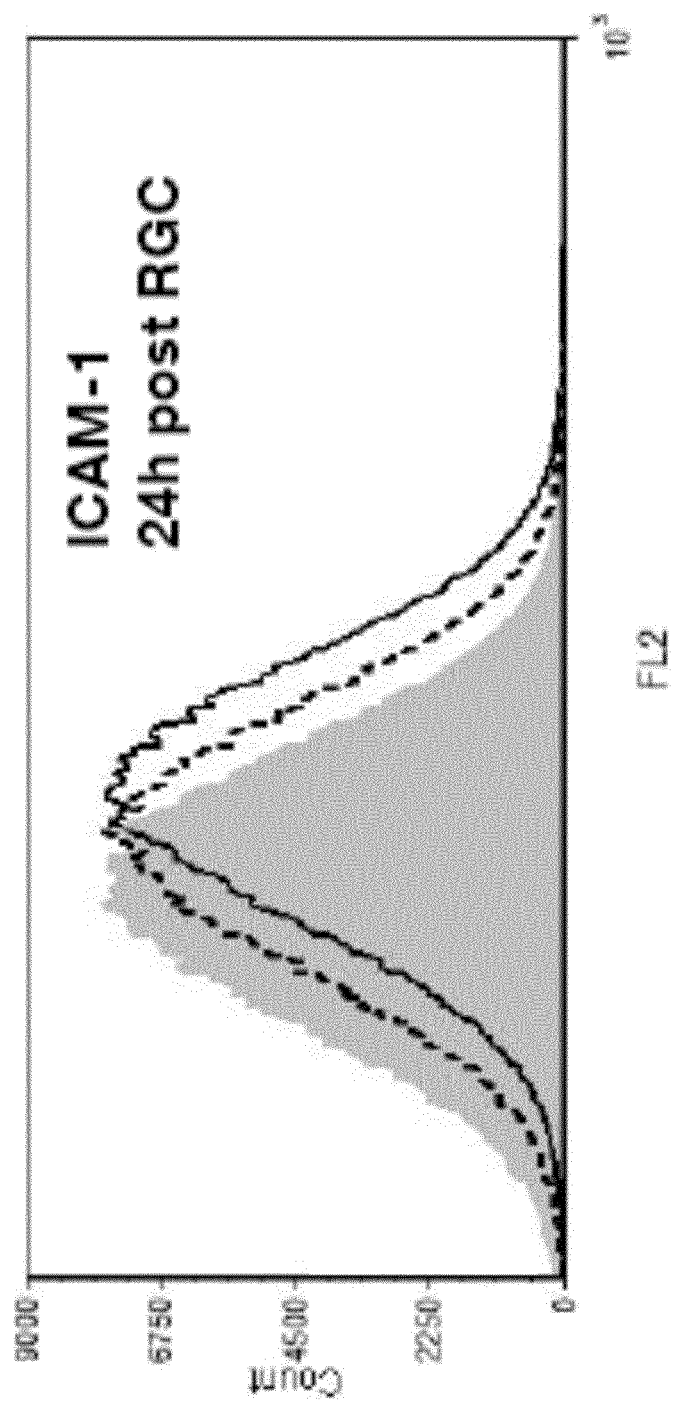
Figure 17E:
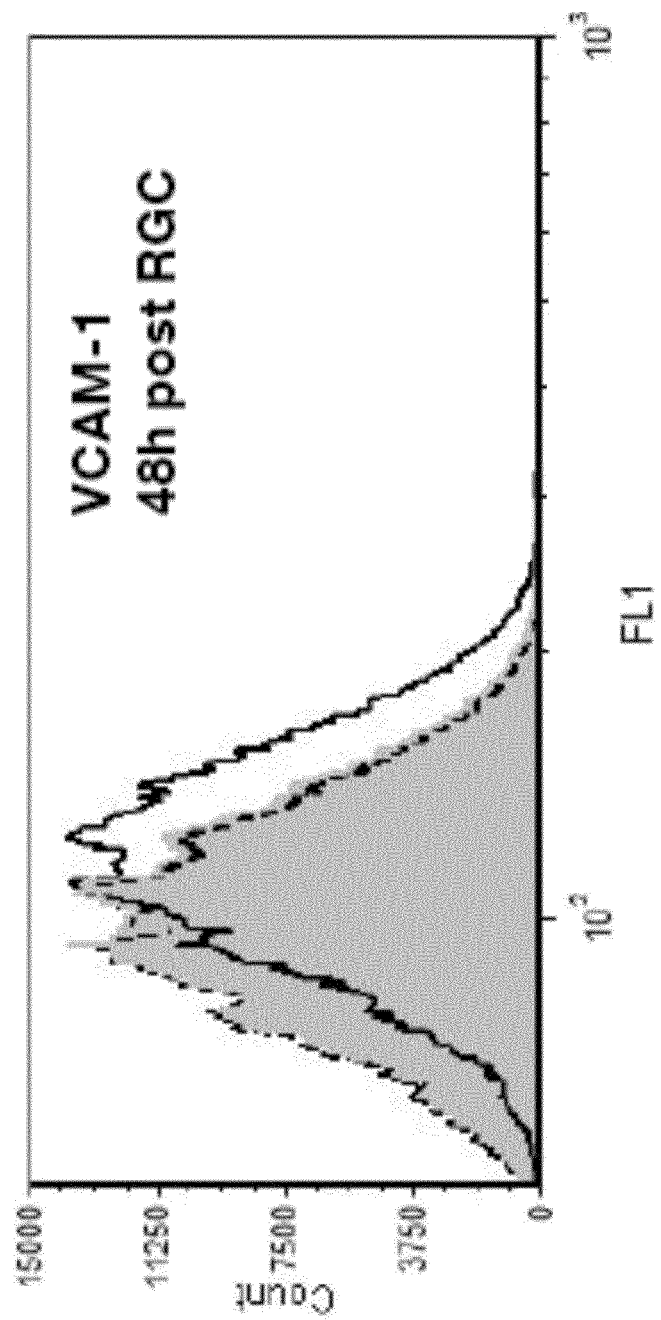

It has further been demonstrated according to the invention that dsRNA constructs as described herein lead to strong expression of selectins and integrins in HUVECs upon transfection with dsRNAs according to the present disclosure. Without being bound to any specific theory, the underlying mechanism is presumably the over-expression of surface TLR-3 upon uptake of the dsRNA construct, followed by restimulation of surface TLR-3 by circulating dsRNA constructs; cf. FIGS. 17 and 18. Thus, at 4 hours post transfection of HUVECs with the dsRNA construct, an increased expression of endosomal and surface TLR-3, together with an increased IP-10 secretion and expression of E-selectin was observed (FIG. 17C). By further stimulating the cells with the dsRNA construct (not transfected into the cells) at 4 hours post transfection, expression of ICAM-1 was observed after 24 hours (FIG. 17D). By further stimulating the cells with the dsRNA construct (again, not transfected into the cells) at 24 hours post transfection, expression of VCAM-1 was observed after 24 hours (FIG. 17E). These data imply that it is the binding of surface TLR-3 to circulating dsRNA constructs and the secretion of IP-10 upon the first stimulation using the transfected dsRNA construct that leads to the expression of selectins and integrins on endothelial cells. Thus, the present invention provides a totally new concept for activation of endothelial cells by TLR-3 agonists in that an antibody-coupled dsRNA construct as described herein could be used for targeted activation of cells such as endothelial cells, which can than be further stimulated by circulating TLR-3 agonists (which could be again a modified dsRNA construct as described herein or an unmodified dsRNA such as those corresponding to the unmodified dsRNA construct and/or another TLR-3 agonist known in the art).

The invention claimed is:

1. A double-stranded ribonucleic acid (dsRNA) of at least 45 bp, optionally having at least one free 5'-triphosphate group, and comprising at least one covalent modification at a 3' end, a 5' end and/or a non-terminal nucleotide, said modification having the structure of general formula (I)

$$X-R^1-Y \quad (I)$$

wherein X represents a 5'- terminal phosphate group, a 3'-terminal phosphate group or a base of a non-terminal nucleotide of the dsRNA;

$R^1$ is selected from the group consisting of a linear or branched $(C_{1-8})$-alkyl group, a linear or branched $(C_{2-8})$-alkenyl group, a linear or branched $(C_{2-8})$-alkinyl group, $-[O-CH_2-CH_2]_m$ with m being an integer of 1 to 20 and a carbohydrate, each of which may be substituted by one or more substituents selected from the group consisting of hydroxyl, oxo, halogen, cyano, $(C_{1-3})$-alkyl, $(C_{1-3})$-alkylhydroxyl, $(C_{2-3})$-alkenyl and $(C_{2-3})$-alkenylhydroxyl;

Y is selected from the group consisting of $NR^2R^3$, $OR^4$ and $SR^5$;

wherein $R^2$, $R^3$, $R^4$ and $R^5$ are each independently selected from the group consisting of hydrogen and a carrier group enabling the uptake of the dsRNA into a cell, which carrier group is optionally bound via a linker group to which the carrier group is bound covalently or non-covalently;

and wherein said covalent modification is not at said at least one free 5'-triphosphate group, if present.

2. The dsRNA of claim 1 wherein one of $R^2$ and $R^3$ in $NR^2R^3$ is hydrogen.

3. The dsRNA of claim 1 wherein $R^2$ and $R^3$ in $NR^2R^3$ are hydrogen.

4. The dsRNA of claim 3 wherein the modification of the dsRNA is selected from a structure of the group consisting of formulas (II), (V) and (VII):

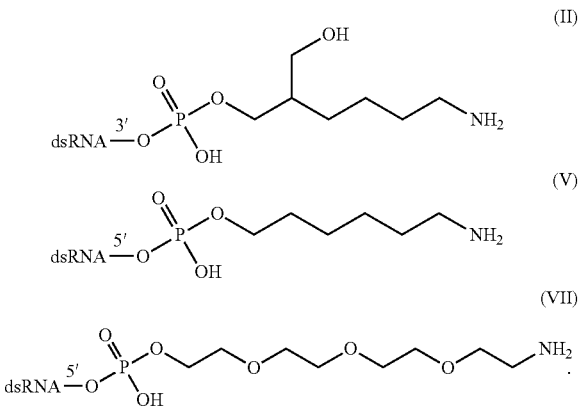

5. The dsRNA according to claim 1 wherein said carrier group is selected from the group consisting of an aptamer, a nucleic acid, a polyethylene glycol group, a peptide, a palmitoyl group, a cholesterol group, a phospholipid, a liposome, a protein, and a partner of a non-covalent binding pair.

6. The dsRNA of claim 5 wherein the modification of the dsRNA containing a polyethylene glycol group is a structure of formula (IV):

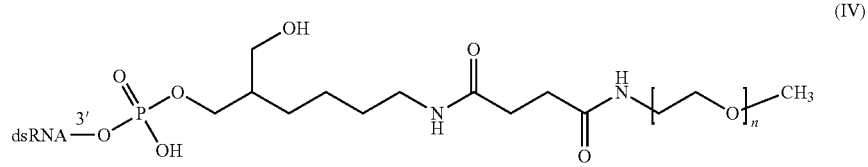

with n being selected such that the average molecular weight of the polyethylene glycol group is from 500 to 1000 Da.

7. The dsRNA of claim 5 wherein the partner of a non-covalent binding pair is selected from biotin and digoxigenin.

8. The dsRNA of claim 7 wherein the modification of the dsRNA is selected from a structure of the group consisting of formulas (III), (VI) and (VIII):

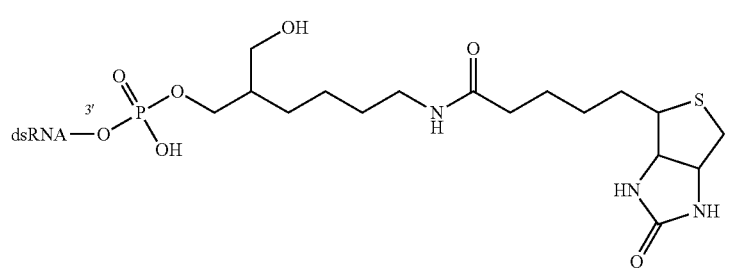
(III)
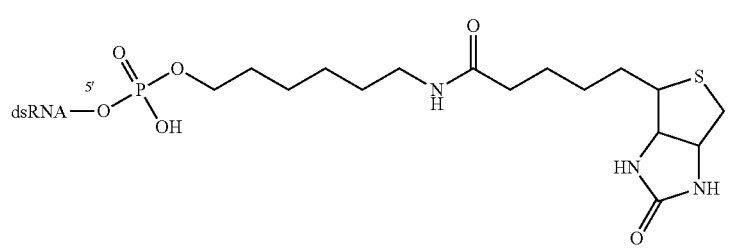
(VI)
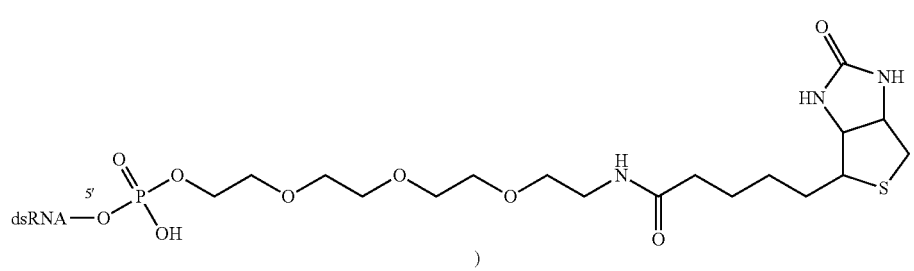
(VIII)
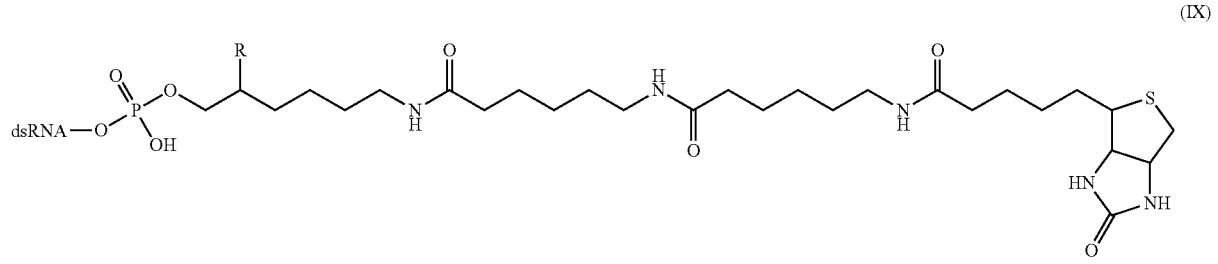
(IX)
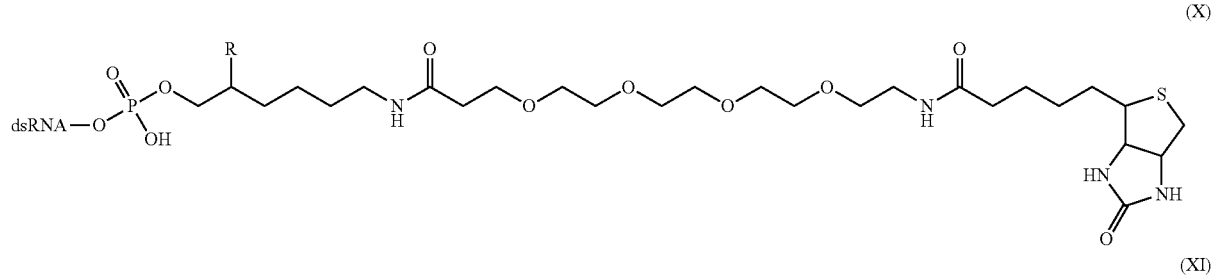
(X)
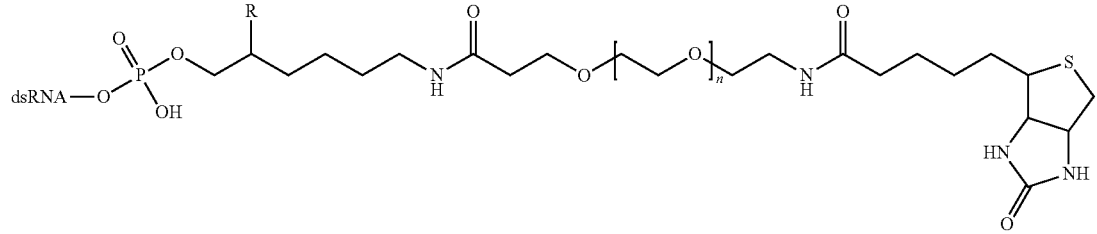
(XI)
wherein R in formulas (IX) to (XI) is selected from H and —CH$_2$OH.
9. The dsRNA of claim 5 wherein the protein is an antibody.
10. The dsRNA according to claim 1 wherein the dsRNA is selected from the group consisting of poly(G):poly(C) and poly(G/I):poly(C), optionally containing one or more modified or unmodified nucleotides.

11. The dsRNA of claim 10 containing at least one amino-allyl-uridine.

12. The dsRNA according to claim 1 having 50 to 200 bp.

13. The dsRNA of claim 12 having 50, 75, 100, 150 or 200 bp.

14. A method for the preparation of a dsRNA comprising a double-stranded ribonucleic acid (dsRNA) of at least 45 bp, optionally having at least one free 5'-triphosphate group, and comprising at least one covalent modification at a 3' end, a 5' end and/or a non-terminal nucleotide, said modification having the structure of general formula (I)

wherein X represents a 5'- terminal phosphate group, a 3'-terminal phosphate group or a base of a non-terminal nucleotide of the dsRNA;

$R^1$ is selected from the group consisting of a linear or branched $(C_{1-8})$-alkyl group, a linear or branched $(C_{2-8})$-alkenyl group, a linear or branched $(C_{2-8})$-alkinyl group, —$[O—CH_2—CH_2]_m$ with m being an integer of 1 to 20 and a carbohydrate, each of which may be substituted by one or more substituents selected from the group consisting of hydroxyl, oxo, halogen, cyano, $(C_{1-3})$-alkyl, $(C_{1-3})$-alkylhydroxyl, $(C_{2-3})$-alkenyl and $(C_{2-3})$-alkenylhydroxyl;

Y is selected from the group consisting of $NR^2R^3$, $OR^4$ and $SR^5$;

wherein $R^2$, $R^3$, $R^4$ and $R^5$ are each independently selected from the group consisting of hydrogen and a carrier group enabling the uptake of the dsRNA into a cell, which carrier group is optionally bound via a linker group to which the carrier group is bound covalently or non-covalently;

wherein said covalent modification is not at said at least one free 5'-triphosphate group, if present, comprising coupling the $R_1$—Y group to a 5'- terminal phosphate group, a 3'-terminal phosphate group or a base of a non-terminal nucleotide of the dsRNA.

15. A pharmaceutical composition comprising:

a double-stranded ribonucleic acid (dsRNA) of at least 45 bp, optionally having at least one free 5'-triphosphate group, and comprising at least one covalent modification at a 3' end, a 5' end and/or a non-terminal nucleotide, said modification having the structure of general formula (I)

wherein X represents a 5'- terminal phosphate group, a 3'-terminal phosphate group or a base of a non-terminal nucleotide of the dsRNA;

$R^1$ is selected from the group consisting of a linear or branched $(C_{1-8})$-alkyl group, a linear or branched $(C_{2-8})$-alkenyl group, a linear or branched $(C_{2-8})$-alkinyl group, —$[O—CH_2—CH_2]_m$ with m being an integer of 1 to 20 and a carbohydrate, each of which may be substituted by one or more substituents selected from the group consisting of hydroxyl, oxo, halogen, cyano, $(C_{1-3})$-alkyl, $(C_{1-3})$-alkylhydroxyl, $(C_{2-3})$-alkenyl and $(C_{2-3})$-alkenylhydroxyl;

Y is selected from the group consisting of $NR^2R^3$, $OR^4$ and $SR^5$;

wherein $R^2$, $R^3$, $R^4$ and $R^5$ are each independently selected from the group consisting of hydrogen and a carrier group enabling the uptake of the dsRNA into a cell, which carrier group is optionally bound via a linker group to which the carrier group is bound covalently or non-covalently;

and wherein said covalent modification is not at said at least one free 5'-triphosphate group, if present; and at least one pharmaceutically acceptable carrier, excipient and/or diluent.

16. The pharmaceutical composition of claim 15 further comprising an antigen.

17. The pharmaceutical composition of claim 15 further comprising an adjuvant.

18. The dsRNA according to claim 1 for use as a medicament.

19. The dsRNA according to claim 1 for use in immunostimulation in a subject.

20. The dsRNA according to claim 1 for use in inducing an anti-viral, anti-bacterial, anti-parasitical and/or cancer and/or anti-tumor response in a subject.

21. The dsRNA according to claim 1, optionally in combination with an antigen, for use as a prophylactic or therapeutic vaccine.

22. A method for immunostimulation in a subject, comprising the step of administering an effective amount of a pharmaceutical composition comprising a double-stranded ribonucleic acid (dsRNA) of at least 45 bp, optionally having at least one free 5'-triphosphate group, and comprising at least one covalent modification at a 3' end, a 5' end and/or a non-terminal nucleotide, said modification having the structure of general formula (I)

wherein X represents a 5'- terminal phosphate group, a 3'-terminal phosphate group or a base of a non-terminal nucleotide of the dsRNA;

$R^1$ is selected from the group consisting of a linear or branched $(C_{1-8})$-alkyl group, a linear or branched $(C_{2-8})$-alkenyl group, a linear or branched $(C_{2-8})$-alkinyl group, —$[O—CH_2\text{-}CH_2]_m$ with m being an integer of 1 to 20 and a carbohydrate, each of which may be substituted by one or more substituents selected from the group consisting of hydroxyl, oxo, halogen, cyano, $(C_{1-3})$-alkyl, $(C_{1-3})$-alkylhydroxyl, $(C_{2-3})$-alkenyl and $(C_{2-3})$-alkenylhydroxyl;

Y is selected from the group consisting of $NR^2R^3$, $OR^4$ and $SR^5$;

wherein $R^2$, $R^3$, $R^4$ and $R^5$ are each independently selected from the group consisting of hydrogen and a carrier group enabling the uptake of the dsRNA into a cell, which carrier group is optionally bound via a linker group to which the carrier group is bound covalently or non-covalently;

wherein said covalent modification is not at said at least one free 5'-triphosphate group, if present, and at least one pharmaceutically acceptable carrier, excipient and/or diluent to the subject.

23. The method of claim 22 wherein the pharmaceutical composition is administered by sub-cutaneous, intra-ocular, intra-cerebral, intra-cerebrospinal, intra-muscular, intra-dermal and/or intra-venous injection in a single or repeated dose.

24. The method of claim 22 wherein the method further comprises administering to the subject an antigen wherein the antigen is present in said pharmaceutical composition or is present in a separate composition which is administered simultaneously or sequentially to said pharmaceutical composition.

25. The method of claim 24 wherein the method further comprises administering to the subject a further adjuvant, optionally in a depot form, wherein the adjuvant may be present in said pharmaceutical composition, in said separate antigen composition or in a further separate composition which is administered simultaneously or sequentially to the pharmaceutical composition and/or the antigen composition.

26. The method according to claim 22 wherein the method further comprises administering at least one further agonist of a Toll-like receptor selected from the group consisting of TLR1 to TLR10.

27. The dsRNA of claim 8, wherein R is H if the phosphate group is a 3'-terminal phosphate group, or R is —CH$_2$OH if the phosphate group is a 5'-terminal phosphate group.

* * * * *